US007981671B2

(12) United States Patent
Charneau et al.

(10) Patent No.: US 7,981,671 B2
(45) Date of Patent: *Jul. 19, 2011

(54) USE OF TRIPLEX STRUCTURE DNA IN TRANSFERRING NUCLEOTIDE SEQUENCES

(75) Inventors: Pierre Charneau, Paris (FR); Véronique Zennou, Paris (FR); Hüseyin Firat, Paris (FR)

(73) Assignee: Institut Pasteur, Paris (FR)

( * ) Notice: Subject to any disclaimer, the term of this patent is extended or adjusted under 35 U.S.C. 154(b) by 478 days.

This patent is subject to a terminal disclaimer.

(21) Appl. No.: 12/153,959

(22) Filed: May 28, 2008

(65) Prior Publication Data

US 2010/0221820 A1 Sep. 2, 2010

Related U.S. Application Data

(63) Continuation of application No. 10/602,663, filed on Jun. 25, 2003, now abandoned, which is a continuation of application No. 09/688,990, filed on Oct. 17, 2000, now Pat. No. 6,682,907, which is a continuation of application No. PCT/FR99/00974, filed on Apr. 23, 1999.

(30) Foreign Application Priority Data

Apr. 24, 1998 (FR) ..................................... 98 05197

(51) Int. Cl.
*C12N 15/00* (2006.01)
*A61K 39/12* (2006.01)
*C12Q 1/70* (2006.01)
(52) U.S. Cl. ... 435/320.1; 435/5; 424/199.1; 424/204.1; 424/207.1
(58) Field of Classification Search .................. None
See application file for complete search history.

(56) References Cited

U.S. PATENT DOCUMENTS

| 6,682,907 B1 | 1/2004 | Charneau et al. |
| 2004/0081636 A1 | 4/2004 | Charneau et al. |

FOREIGN PATENT DOCUMENTS

| EP | 0 611 822 A2 | 8/1994 |
| WO | WO 97/12622 A1 | 4/1997 |
| WO | WO 9712622 A1 * | 4/1997 |
| WO | WO 97/32983 A1 | 9/1997 |
| WO | WO 98/39463 A2 | 9/1998 |
| WO | WO 98/46083 A1 | 10/1998 |
| WO | WO 00/31280 A2 | 6/2000 |

OTHER PUBLICATIONS

Charneau et al. A Second Origin of DNA Plus-Strand Synthesis Is Required for Optimal Human Immunodeficiency Virus Replication. Journal of Virology 1992, vol. 66, No. 5, p. 2814-2820.*
Parolin, C., Analysis in Human Immunodeficiency Virus Type 1 Vectors of cis-Acting Sequences That Affect Gene Transfer into Human Lymphocytes. Journal of Virology Jun. 1994, vol. 68, No. 6, p. 3888-3895.

Zufferey et al., Multiply attenuated lentiviral vector achieves efficient gene delivery in vivo; Nature Biotechnology, vol. 15, (1997) 871-875.
Charneau et al, HIV-1 Reverse Transcription, A termination step at the center of the genome; J. Mol. Biol. (1994) 241, 651-662.
Charneau et al., A single-stranded gap in human immunodeficiency virus unintegrated linear DNA defined by a central the polypurine tract; J. Virol. (1991) 65, 2415-2421.
Charneau et al., A second origin of DNA plus-strand synthesis is required for optimal human immunodeficiency virus replication; J. Virol. (1992) 66, 2814-2820.
Erlwein et al., Sequences in pol are required for transfer of human foamy virus-based vectors; J. Virol. (1998) 72, 5510-5516.
Naldini et al, Efficient transfer, integration, and sustained long-term expression of the transgene in adult rat brains injected with a lentiviral vector; Proc. Natl. Acad. Sci. USA, (1996) vol. 93, 11382-11388.
Naldini et al, In vivo gene delivery and stable transduction of nondividing cells by a lentiviral vector; Science, vol. 272, (1996) 263-267.
Poznansky et al., Gene transfer into human lymphocytes by a defective human immunodeficiency virus type 1 vector; J. Virol. (1991) 65, 532-536.
Stetor et al., Characterization of (+) strand initiation and termination sequences located at the center of the equine infectious anemia virus genome; Biochem. (1999) vol. 38, 3656-3667.
Kim et al.; Temporal aspects of DNA and RNA synthesis during human immunodeficiency virus infection: Evidence for differential gene expression; J. Virol. (1989) 63, 3708-3713.
Goldman et al.; Lentiviral vectors for gene therapy of cystic fibrosis; Human Gene Therapy (1997) 8, 2261-2268.
European Patent Office, Search reports issued in the corresponding French and PCT applications Nos. 9805197 and PCT/FR00974.
Giovannangeli et al, Accessibility of nuclear DNA to triplex-forming oligonucleotides: The integrated HIV-1 provirus as a target. Proceedings National Academy of Science, U.S.A., Jan. 1997, vol. 94, pp. 79-84.
Batra et al., Transduction of Non-Small Cell Lung Cancer Cells by Adenoviral and Retroviral Vectors, Am. J. Respir. Cell Mol. Biol., (1998) 18:402-410.
Blomer, U., et al., Abstract In-vitro and In-vivo Study of Gene Transfer with a New HIV Derived Vector, Zentralbl Neurochir Supplement (1996).
Johnson et al., Effect of Host Modification and Age on Airway Epithelial Gene Transfer Mediated by a Murine Leukemia Virus-Derived Vector, Journal of Virology, (1998) 72(11):8861-8872.
Matukonis et al, "Development of Second- and Third-Generation Bovine Immunodeficiency Virus-Based Gene Transfer Systems," Human Gene Therapy (2002) 13:1293-1303.
Molina et al.,"Mapping of Bovine Immunodeficiency Virus Packaging Signal and RRE and Incorporation into a Minimal Gene Transfer Vector," Virology (2002) 304:10-23.

(Continued)

*Primary Examiner* — Zachariah Lucas
*Assistant Examiner* — Louise Humphrey
(74) *Attorney, Agent, or Firm* — Law Office of Salvatore Arrigo and Scott Lee, LLP

(57) ABSTRACT

The invention concerns a recombinant vector characterized in that it comprises a polynucleotide comprising a central initiation cis-active region (cPPT) and a termination cis-active region (CTS) of retroviral or retroviral-like origin, further comprising a predetermined nucleotide sequence (transgene or nucleotide sequence of interest) and retrotranscription regulating, expressing and packaging signals of retroviral or retroviral-like origin.

24 Claims, 32 Drawing Sheets

OTHER PUBLICATIONS

Negre, D., ETA/., "Characterization of Novel Safe Lentiviral Vectors Derived from Simian Immunodeficiency Virus (SIV mac251) that Efficiently Transduce Mature Human Dendritic Cells," Gene Therapy (2000) 7:1613-1623.

Olsen, JC, "Gene transfer vectors derived from equine infectious anemia virus," Gene Therapy (1998) 5:1481-1487.

Poeschla et al. "Efficient transduction of nondividing human cells by feline immunodeficiency virus lentiviral vectors," Nature Medicine (1998) 4(3) 354-357.

Poeschla et al. "Identification of a Human Immunodeficiency Virus Type 2 (HIV-2) Encapsidation Determinant and Transduction of Nondividing Human Cells by HIV-2-Based Lentivirus Vectors," Journal of Virology (1998) 72(8) 6527-6536.

Sirven, "The human immunodeficiency virus type-1 central DNA Flap is a crucial determinant for lentiviral vector nuclear import and gene transduction of human hematopoietic stem cells," Blood (2000) 92(13) 4103-4110.

Riggs et al., A Novel Human Amphotropic Packaging Cell Line: High Titer, Complement Resistance, and Improved Safety, Virology 218, 290-295 (1996).

* cited by examiner

REVERSE TRANSCRIPTION OF LENTIVIRUSES, FORMATION OF CENTRAL DNA TRIPLEX

PLASMIDS USED FOR THE PRODUCTION OF HIV VECTOR PARTICLES

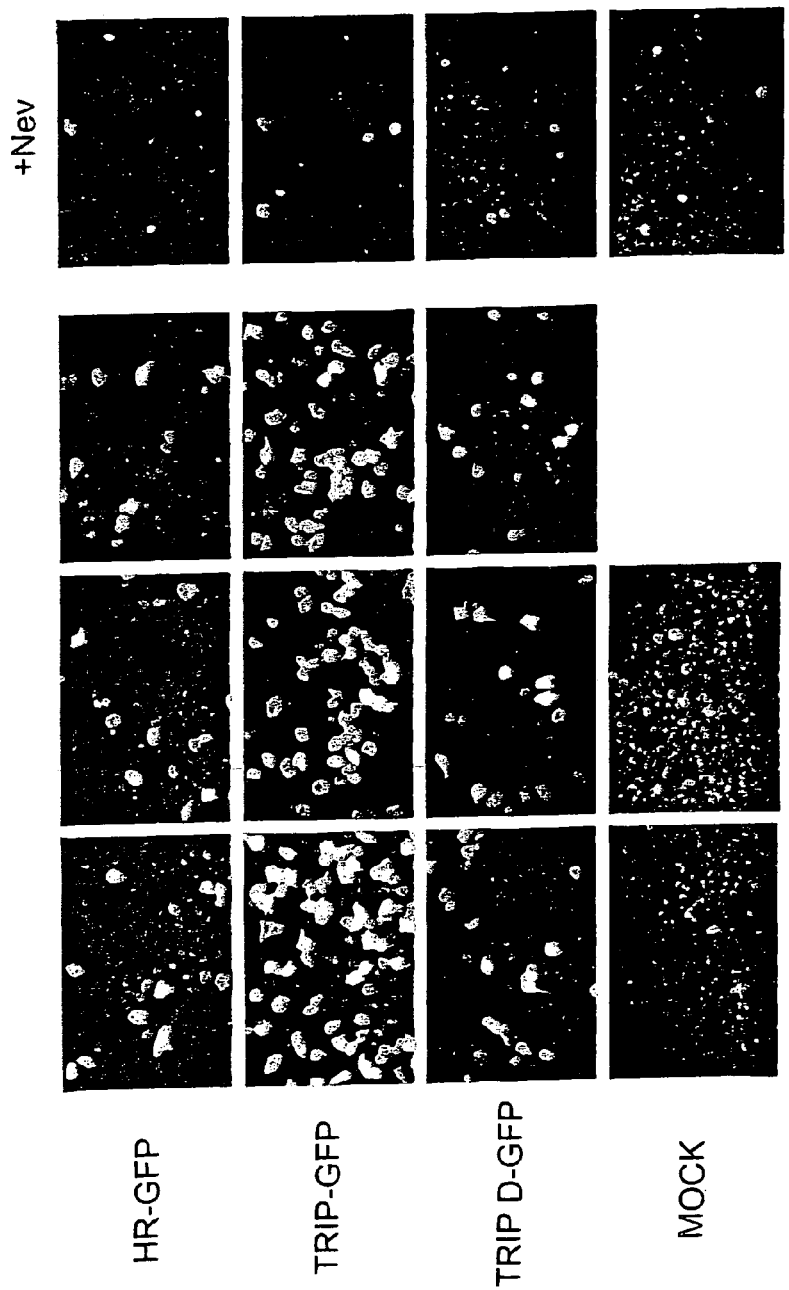

QUANTIFICATION OF DEGREE OF TRANSDUCTION OF EGFP GENE
BY HIV VECTORS WITH OR WITHOUT TRIPLEX

TRANSDUCTION OF GFP IN MITOTIC HeLa CELLS

TRANSDUCTION OF GFP IN BLOCKED HeLa CELLS

IMPACT OF CENTRAL TRIPLEX ON TRANSDUCTION OF GFP GENE IN RAT PRIMARY SPINAL CELLS

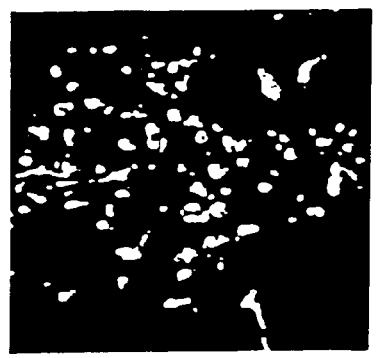
TRIP GFP
HR GFP
IMPACT OF CENTRAL TRIPLEX ON TRANSDUCTION OF GFP GENE IN RAT PRIMARY SPINAL CELLS
FIG. 6B

FIG. 7A.1
IMPACT OF TRIPLEX ON IN VIVO TRANSDUCTION OF EGFP GENE IN RAT BRAIN: TRANSDUCTION AT INJECTION SITE

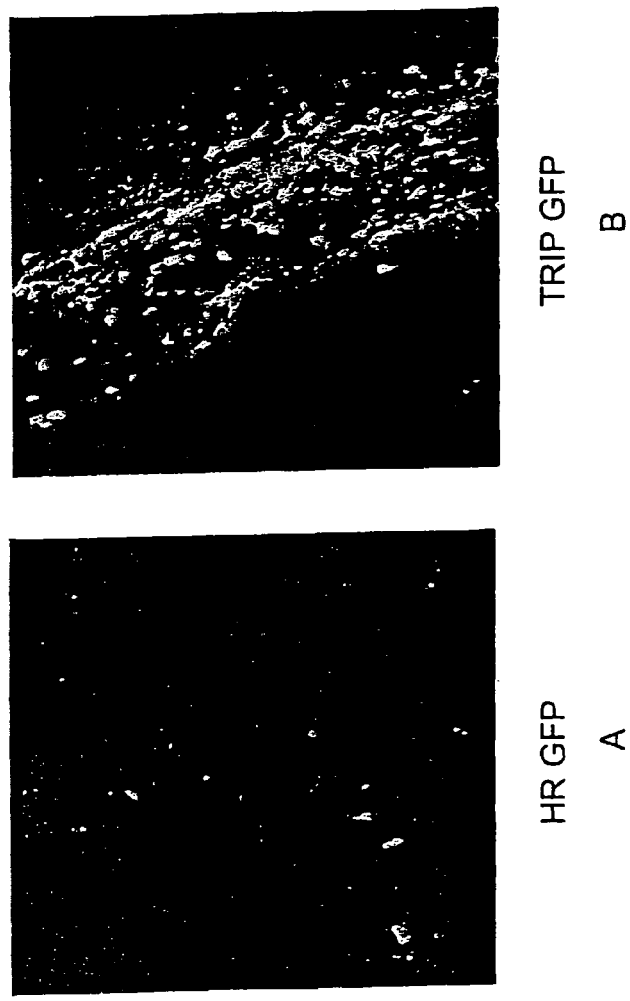
FIG. 7A.2
IMPACT OF TRIPLEX ON IN VIVO TRANSDUCTION OF GFP GENE IN RAT BRAIN

Figure 8B:
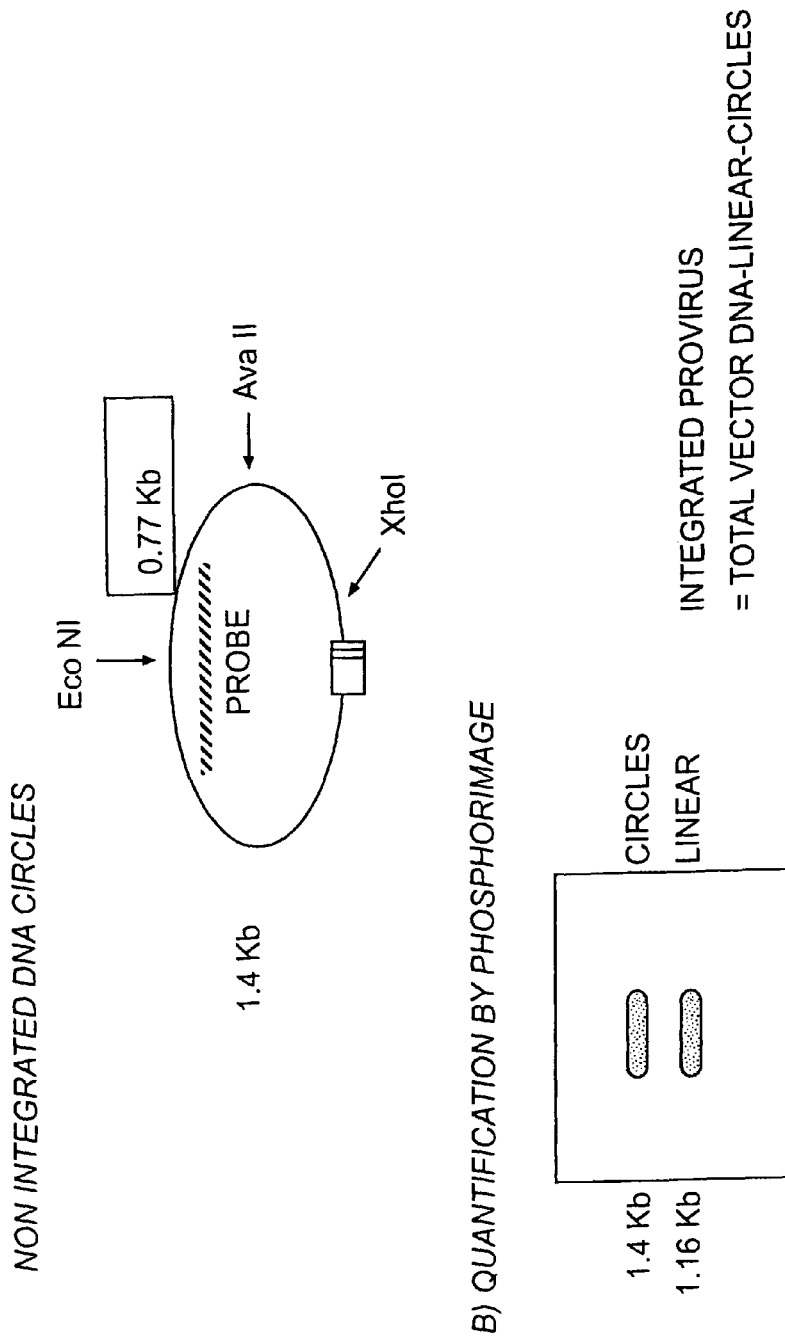

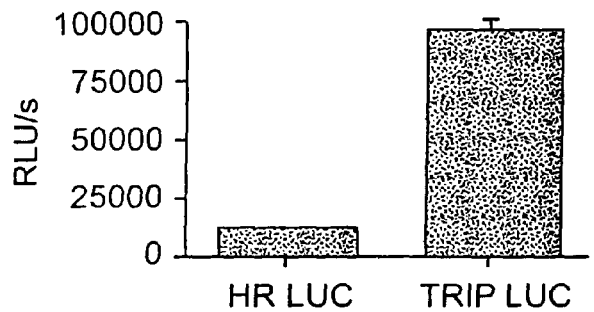
FIG. 7B.1 IMPACT OF TRIPLEX ON TRANSDUCTION OF LUCIFERASE ACTIVITY IN HeLa CELLS IN VITRO
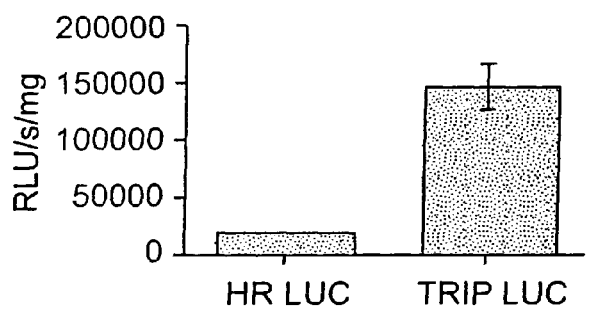
FIG. 7B.2 IMPACT OF TRIPLEX ON TRANSDUCTION OF LUCIFERASE ACTIVITY IN RAT BRAIN IN VIVO
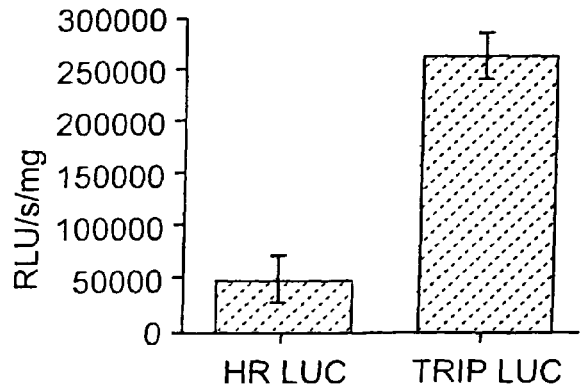
FIG. 7B.3 IMPACT OF TRIPLEX ON TRANSDUCTION OF LUCIFERASE ACTIVITY IN MOUSE BRAIN CELLS IN VIVO METHOD FOR QUANTITATIVE ANALYSIS OF MATURATION OF VECTOR DNA
A) SOUTHERN BLOT STRATEGY
*LINEAR DNA*
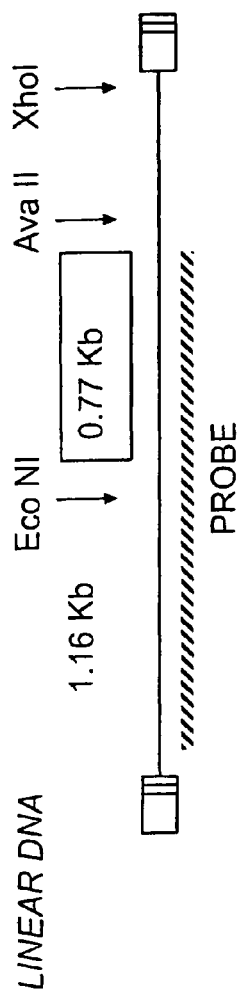
*INTEGRATED PROVIRUS*
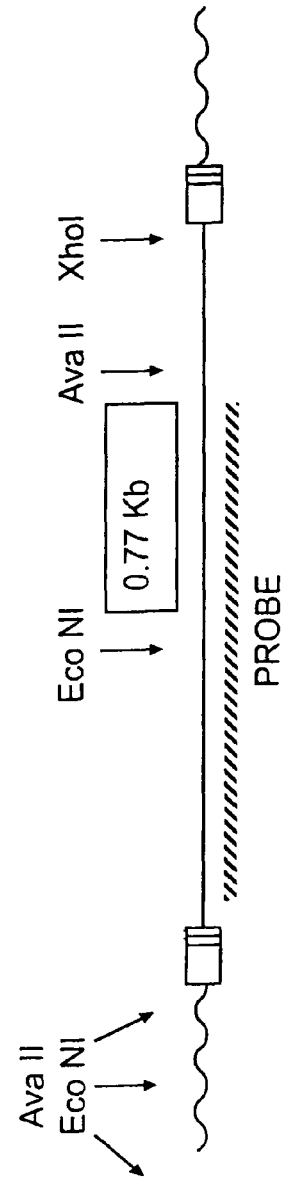
FIG. 8A

ANALYSIS OF NUCLEAR IMPORT OF VECTOR DNA

HIV A TRIPLEX VECTOR: TRIP-EGFP

TRIPLEX CAEV (CAPRINE ARTHRITIS ENCAPHALITIS VIRUS)

```
                                              BspW I
                                              Fnu4H I
         Tfi I      Fnu4H I
         Hinf I    BspW I   Bbv I  Bbv I  Rma I
        Sfe I    |   |   |     |   ·|  |  |
        | | |    |  21   |     | 38 41  | 47
gttccagccacaatttgtgctgctgtagaatcagcagccatagcagcagccctagtgcctataaataaagaagaaggtgggctgggacaagccctatggat  100
caaggtcggtgttaaacagcagacgacatcttagtcgtcgtcgggatcagcggtatcgtcgtcgggatcagcggtattatatttctttcccaccgaccccctgttcggatacta
        |        |   |        |     |   |
        |       26  32       38    41  44
                                      ·
                                     cPPT
```

```
                                                                        Mnl I
                                                                        |
atttttatatataataagaacagaaagaataataataaagaatatataaatttcaaaaaattcaattctgtgtgttattacagaataaggaaaagaggac  200
taaaatatatattttcttgtctttttattattatatttaaagagttttaagttaagacaataatgtcttattcctttcctg
                                                                                |
                                                                               195
```

<<CTS>>

*FIG. 11A*

TRIPLEX EIAV (EQUINE INFECTIOUS ANAEMIA VIRUS)

```
         Mae III       Mn

TRIPLEX VISNA

```
           Mnl I
Sau96 I                                    Rma I                                          Mse I
Nla IV
Ava II
GGACCCTCATTACTTCTAAATATAaaaagaaagggTGGGCTAGGGACAAGCCCTATGGATATATTTATATTTAATAAGGAACAACAAGAATACAGCAACA  100
CCTGGGAGTAATGAGATTTATATtttttcccACCCGATCCCGTTCGGGATACCTATATAAATATAAATTATTCCTTGTTGTTTCTTATGTCGTTGT
1                                       39                                               70
1
1       cPPT
1
5
```

```
                                                            ScrF I
                                                            EcoR II
                                                            Dsa V
                                                            BstX I
                                                            BstN I                          Sau96 I    Rsa I
                                                 Fok I                                      Ava II     Csp6 I
         Xmn I  Taq I                            SfaN I                                     ──────     ──────
         ─────  ─────                      Mnl I BstK I
AAGTAAATCaaaacaagaaaaattcGATTTTGTTATTACAGAACAAGAAAAAGAGGCATCCAGGAGAGTGGCAAGGACCAACACAGTACTTTGGGGC  200
TTCATTTAGTtttgttctttttaagCTAAAACAATAACATGTCTTGTTCTTTTCTCCGTAGGTCCTCTCACCGTTCCTGGTTGTGTCCATGAAACCCCG
         117    125                        154  158    162                                 177        189
                                                 159    162                                177        189
 <<CTS>>                                                162
                                                        162
                                                        162
```

FIG. 11C

TRIPLEX SIV_AGM (SIMIAN IMMUNODEFICIENCY VIRUS)

```

TRIPLEX HIV-2 RID (HUMAN IMMUNODEFICIENCY VIRUS)

```
                                        Hph I
                                        Sau3A I
                                        Mbo I
                                        Dpn II
                    Ple I      Mse I    Dpn I                              Mnl I
 Mse I              HinF I     Ase I    Bcl I
 Dra I
Nla III
tgcatgaatttaaaagaaggggggggaataggggaatatgactccatcagaaagattaatcaatatgattcaccacagaacaagagatacaattcctccaag  100
acgtacttaaatttcttccccccccttatccccttatactgaggtagtctttctaattagttatactagtgtggtgtcttgttctctatgttaaggaggttc
     -                  -                  -                  -                  -
     3                  39                 54                 65                 93
     10                 39                 55                 66
     11                                    66
cPPT                                       66
                                           68
```

*FIG. 11E*

TRIPLEX HIV-2 RID (HUMAN IMMUNODEFICIENCY VIRUS)

```
                                                                ScrF I
                                                                EcoR II
                                                                Dsa V
                                                                BstN I
                                                                BstK I
                                                                BsaJ I
                                            Sau3A I             Sau96 I
                                            Mbo I               Ava II
                                            Dpn II              PpuM I
          Mse I                             Dpn I               EcoO109 I
          |                                 |                   |
ccaaaaattcaaaattaaagatttcgggtctattcagagaaggcagagatcagttgtggaaaggacctgggaactactgtggaaaggagaaggagc  200
ggtttttaagtttttaatttctaaagccagatataaagtcttctccgtctctagtcaactagtcaacaccttcctgaccccttgatgacaccttcctttcctcg
           -                                -                   -       -
           115                              151                 165     169
                                            151                 165     169
<<CTS>>                                     151                 166     169
                                            151                 166     169
```

FIG. 11E (cont)

TRIPLEX HIV-1 LAI

```
         Fok I       Mse I                                            Rsa I    Bsq I
                     Dra I                                            Csp6 I   Acc I
CAGTATTCATCCACAATTTAAAAGAAAAGGGGGGATTGGGGGGTACAGTGCAGGGGAAAGAATAGTAGACATAAGTGCAACAGACATACAAACTAAAGA  100
GTCATAAGTAGGTGTTAAAATTTTCTTTTCCCCCCCTAACCCCCCATGTCACGTCCCCTTTCTTATCATCTGTATTATCGTTGTCTGTATGTTGATTTCT
         :         :         :         :         :         :         :         :         :         :
         8         18                                                 44       49
                   19                                                 44
                   cPPT                                                        66
```

```
                                                                              Sau96 I   Mnl I
         Sau3A I                                                              Ava II    Alu I
         Mbo I
         Dpn II
         Dpn I
         Alw I
         BstY I
ATTACAAAAAACAAATTACaaaaattcaaaattttCGGGTTTATTACAGGGACAGCAGAGATCCACTTTGGAAAGACCAGCAAAGCTCCTCTGGAAAGGT  200
TAATGTTTTTTGTTTAATGTttttaagttttaaaaGCCCAAATAATGTCCCTGTCGTCTCTAGGTGAAACCTTTCGTTTCGAGGAGACCTTTCCA
         :         :         :         :         :         :         :         :         :         :
         158                                                         174       184
         159                                                         174       188
         159
         159
         159
         159

<<CTS>>
```

FIG. 11F

5' [TTTTAAAAGAAAAGGGGG]ATTGcPPT

-GGGGGTACAGTGCAGGGGAAAGAATAG-

-TAGACATAATAGCAACAGACATACAAA-

-CTAAAGAATTA[CAAAAACAAATTAC-

-AAAAATTCAAAATTTTC] 3'

CTS

TRIPLEX DNA REGION OF HIV-1 VIRUS

FIG. 11G

ALIGNMENT OF cPPT AND 3'PPT SEQUENCES
IN SOME LENTIVIRUSES

```
3' PPT       AAAAGAAAAGGGGGG      HIV-1
CENTRAL PPT  **************
             AAAACAAGGGGGGG       HIV-2 ROD
             ****G*********
             AAAAGAAAAGGGGGG      SIV mac & HIV-2 NIH-Z
             *****GGA**A
             AAAAGAAAAGGGAGG      SIVagm
             *******G**AG*A
          AAAAAGAAAAAGAAAGGGTGG   VISNA
          ***T*T***************
          AAAAATAAAAAAGAAAGGGTG   CAEV
          *T**************
             AACAAGGGGGAA         EIAV
             **AGG*A***A**
```

FIG. 11H

RESULTS REPRESENTING THE CYTOTOXIC RESPONSE AFTER IMMUNIZATION (INTRAPERITONEAL) OF HHD MICE BY THE TRIP-MEL-IRES-GFP VECTOR

EPITOPIC PEPTIDES INCLUDED IN MELANOMA POLYEPITOPE

| MELANOMA PEPTIDE | | SEQUENCE | REFERENCE |
|---|---|---|---|
| gp100 | 154-162 | KTWGQYWQV | KAWAKAMI, Y. ET AL. J.IMMUNOL.1995.154:3961-8. |
| | 209-217 | ITDQVPFSV | KAWAKAMI, Y. ET AL. J.IMMUNOL.1995.154:3961-8. |
| | 280-288 | YLEPGPVTA | COX, AL. ET AL. SCIENCE.1994.264:716-9. |
| | 457-466 | LLDGTATLRL | KAWAKAMI, Y. ET AL. J.IMMUNOL.1995.154:3961-8. |
| MART-1 | 27-35 | AAGIGILTV | KAWAKAMI, Y. ET AL. J.IMMUNOL.1995.154:3961-8. |
| | 32-40 | ILTVILGVL | CASTELLI, C. ET AL. J.EXP.MED.1995.181:363-8. |
| TYROSINASE | 1-9 | MLLAVLYCL | WOLFEL, T. ET AL. EUR.J.IMMUNOL.1994.24:759-64. |
| | 368-376-D | YMDGTMSQV | MOSSE, CA. ET AL. J.EXP.MED.1998.187:37-48. |
| GnT-V/NA17-A | nt38-64b | VLPDVFIRC | GUILLOUX, Y. ET AL. J.EXP.MED.1996.183:1173-83. |
| MAGE-3 | 271-279 | FLWGPRALV | VAN DER BRUGGEN, P. ET AL. EUR.J.IMMUNOL.1994.24:3038-43. |

AMINO ACID SEQUENCE OF MELANOMA POLYPITOPE

AAGIGILTVFLWGPRALVMLLAVLYCLLLDGTATLRLKTWGQYWQVYMDGTMSQVITDQVPFSVYLEPGPVTAILTVILGVLVLPDVFIRCV

FIG. 15

SEQUENCE LISTING

<160> NUMBER OF SEQ ID NOS: 33

<210> SEQ ID NO 1
<211> LENGTH: 14
<212> TYPE: DNA
<213> ORGANISM: Lentivirus

<400> SEQUENCE: 1
aacaaaggga ggga                                              14

<210> SEQ ID NO 2
<211> LENGTH: 24
<212> TYPE: DNA
<213> ORGANISM: Lentivirus

<400> SEQUENCE: 2
aaaaaatttt gtttttacaa aatc                                        24

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccggatcccc accggtcgcc acc                                         23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccctcgagct agagtcgcgg ccg                                         23

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gtcgtcggcg ccgaattcac aaatggcagt attcatcc                         38

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtcgtcggcg ccccaaagtg gatctctgct gtcc                             34

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ccagatctac gcgtgccacc atggctgctg gt                               32

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8

```
cggaattcga cctaaacgca acggatg                                              27
```

<210> SEQ ID NO 9
<211> LENGTH: 200
<212> TYPE: DNA
<213> ORGANISM: Caprine arthritis encephalitis virus

<400> SEQUENCE: 9

```
gttccagcca caatttgtcg ctgtagaatc agccatagca gcagccctag tcgccataaa    60
tataaaaaga aagggtgggc tggggacaag ccctatggat attttttatat ataataaaga  120
acagaaaaga ataataata aatataataa aaattctcaa aaaattcaat tctgttatta   180
cagaataagg aaaagaggac                                              200
```

<210> SEQ ID NO 10
<211> LENGTH: 200
<212> TYPE: DNA
<213> ORGANISM: Equine infectious anemia virus

<400> SEQUENCE: 10

```
cttgtaacaa agggagggaa agtatgggag gacagacacc atgggaagta tttatcacta    60
atcaagcaca agtaatacat gagaaacttt tactacagca agcacaatcc tccaaaaaat  120
tttgttttta caaaatccct ggtgaacatg attggaaggg acctactagg gtgctgtgga  180
agggtgatgg tgcagtagta                                              200
```

<210> SEQ ID NO 11
<211> LENGTH: 200
<212> TYPE: DNA
<213> ORGANISM: Lentivirus

<400> SEQUENCE: 11

```
ggaccctcat tactctaaat ataaaaagaa agggtgggct agggacaagc cctatggata    60
tatttatatt taataaggaa caacaaagaa tacagcaaca agtaaatca aaacaagaaa   120
aaattcgatt ttgttattac agaacaagaa aaagagggca tccaggagag tggcaaggac   180
caacacaggt actttggggc                                              200
```

<210> SEQ ID NO 12
<211> LENGTH: 200
<212> TYPE: DNA
<213> ORGANISM: Simian immunodeficiency virus

<400> SEQUENCE: 12

```
tactgatggc ttgcatactt cacaatttta aaagaaaggg aggaataggg ggacagactt    60
cagcagagag actaattaat ataataacaa cacaattaga aatacaacat ttacaaacca  120
aaattcaaaa aattttaaat tttagagtct actacagaga agggagagac cctgtgtgga  180
aaggaccggc acaattaatc                                              200
```

<210> SEQ ID NO 13
<211> LENGTH: 200
<212> TYPE: DNA
<213> ORGANISM: Human immunodeficiency virus

<400> SEQUENCE: 13

```
tgcatgaatt ttaaaagaag gggggaata ggggatatga ctccatcaga aagattaatc    60
aatatgatca ccacagaaca agagatacaa ttcctccaag ccaaaaattc aaaattaaaa  120
gattttcggg tctatttcag agaaggcaga gatcagttgt ggaaaggacc tggggaacta  180
```
ctgtggaaag gagaaggagc                                                    200

<210> SEQ ID NO 14
<211> LENGTH: 200
<212> TYPE: DNA
<213> ORGANISM: Human immunodeficiency virus

<400> SEQUENCE: 14
cagtattcat ccacaatttt aaaagaaaag gggggattgg ggggtacagt gcaggggaaa         60
gaatagtaga cataatagca acagacatac aaactaaaga attacaaaaa caaattacaa        120
aaattcaaaa ttttcgggtt tattacaggg acagcagaga tccactttgg aaaggaccag        180
caaagctcct ctggaaaggt                                                    200

<210> SEQ ID NO 15
<211> LENGTH: 15
<212> TYPE: DNA
<213> ORGANISM: Human immunodeficiency virus

<400> SEQUENCE: 15
aaaagaaaag ggggg                                                          15

<210> SEQ ID NO 16
<211> LENGTH: 14
<212> TYPE: DNA
<213> ORGANISM: Human immunodeficiency virus

<400> SEQUENCE: 16
aaaacaaggg gggg                                                           14

<210> SEQ ID NO 17
<211> LENGTH: 15
<212> TYPE: DNA
<213> ORGANISM: Unknown
<220> FEATURE:
<223> OTHER INFORMATION: Description of Unknown:
      SIV mac or HIV-2NH-Z

<400> SEQUENCE: 17
aaaagaaaag ggggg                                                          15

<210> SEQ ID NO 18
<211> LENGTH: 15
<212> TYPE: DNA
<213> ORGANISM: Simian immunodeficiency virus

<400> SEQUENCE: 18
aaaagaaaag ggagg                                                          15

<210> SEQ ID NO 19
<211> LENGTH: 22
<212> TYPE: DNA
<213> ORGANISM: Lentivirus

<400> SEQUENCE: 19
aaaaagaaaa aagaaagggt gg                                                  22

<210> SEQ ID NO 20
<211> LENGTH: 22
<212> TYPE: DNA
<213> ORGANISM: Caprine arthritis encephalitis virus

<400> SEQUENCE: 20

-continued

```
aaaaataaaa aaagaaaggg tg                                            22
```

<210> SEQ ID NO 21
<211> LENGTH: 13
<212> TYPE: DNA
<213> ORGANISM: Equine infectious anemia virus

<400> SEQUENCE: 21

```
aacaaggggg gaa                                                      13
```

<210> SEQ ID NO 22
<211> LENGTH: 9
<212> TYPE: PRT
<213> ORGANISM: Unknown
<220> FEATURE:
<223> OTHER INFORMATION: Description of Unknown:
      Melanoma peptide

<400> SEQUENCE: 22

Lys Thr Trp Gly Gln Tyr Trp Gln Val
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      Melanoma peptide

<400> SEQUENCE: 23

Ile Thr Asp Gln Val Pro Phe Ser Val
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      Melanoma peptide

<400> SEQUENCE: 24

Tyr Leu Glu Pro Gly Pro Val Thr Ala
1               5

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      Melanoma peptide

<400> SEQUENCE: 25

Leu Leu Asp Gly Thr Ala Thr Leu Arg Leu
1               5                   10

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      Melanoma peptide

<400> SEQUENCE: 26

Ala Ala Gly Ile Gly Ile Leu Thr Val

```
<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      Melanoma peptide

<400> SEQUENCE: 27

Ile Leu Thr Val Ile Leu Gly Val Leu
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      Melanoma peptide

<400> SEQUENCE: 28

Met Leu Leu Ala Val Leu Tyr Cys Leu
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      Melanoma peptide

<400> SEQUENCE: 29

Tyr Met Asp Gly Thr Met Ser Gln Val
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      Melanoma peptide

<400> SEQUENCE: 30

Val Leu Pro Asp Val Phe Ile Arg Cys
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      Melanoma peptide

<400> SEQUENCE: 31

Phe Leu Trp Gly Pro Arg Ala Leu Val
1               5

<210> SEQ ID NO 32
<211> LENGTH: 92
<212> TYPE: PRT
<213> ORGANISM: Artificial Sequence
<220> FEATURE:
<223> OTHER INFORMATION: Description of Artificial Sequence: Synthetic
      Melanoma polyepitope
```

```
<400> SEQUENCE: 32

Ala Ala Gly Ile Gly Ile Leu Thr Val Phe Leu Trp Gly Pro Arg Ala
1               5                   10                  15

Leu Val Met Leu Leu Ala Val Leu Tyr Cys Leu Leu Leu Asp Gly Thr
            20                  25                  30

Ala Thr Leu Arg Leu Lys Thr Trp Gly Gln Tyr Trp Gln Val Tyr Met
        35                  40                  45

Asp Gly Thr Met Ser Gln Val Ile Thr Asp Gln Val Pro Phe Ser Val
    50                  55                  60

Tyr Leu Glu Pro Gly Pro Val Thr Ala Ile Leu Thr Val Ile Leu Gly
65                  70                  75                  80

Val Leu Val Leu Pro Asp Val Phe Ile Arg Cys Val
                85                  90

<210> SEQ ID NO 33
<211> LENGTH: 119
<212> TYPE: DNA
<213> ORGANISM: Human immunodeficiency virus

<400> SEQUENCE: 33
ttttaaaaga aaaggggga ttgggggta cagtgcaggg gaaagaatag tagacataat      60
agcaacagac atacaaacta aagaattaca aaaacaaatt acaaaaattc aaaattttc    119
```

USE OF TRIPLEX STRUCTURE DNA IN TRANSFERRING NUCLEOTIDE SEQUENCES

This is a continuation of Application No. 10/602,663, filed Jun. 25, 2003 (abandoned), which is a continuation of application Ser. No. 09/688,990, filed Oct. 17, 2000, (now U.S. Pat. No. 6,682,907), which is a continuation of PCT/FR99/00974, filed Apr. 23, 1999, which claims priority of FR 98/05197, filed Apr. 24, 1998, all of which are incorporated herein by reference.

The present application relates to the use of DNA sequences which are capable of having a triple-stranded structure or organisation (known as triplex DNA) for transferring nucleotide sequences into cells, and to recombinant vectors containing such triplex sequences.

Thus the invention concerns the definition and provision of novel means which can be used, for example, in the context of protocols for gene therapy or transgenesis for the production of transgenic animals or plants or recombinant cells or cell lines. Such means comprise producing novel vectors which can transfer a nucleotide sequence, in particular a sequence of therapeutic interest, into target cells in the human or animal body.

An important limitation to current gene therapy approaches lies in the vectorisation of the gene of therapeutic interest. Retroviral vectors derived from an oncovirus, principally from MoMLV, have been widely used for gene transfer. Their application is largely limited by the fact that oncoviruses only integrate into target cells which are actively dividing. In contrast, lentivirus have the unique capacity among retroviruses of infecting differentiated non mitotic cells and represent viral candidates of interest for the development of novel vectors. While retaining the advantages of an oncoviral vector (absence of immunogenicity, stable integration), lentiviruses could enable in vivo transduction of non mitotic differentiated tissues (brain, muscle, liver, lung . . . ) and could therefore have a wide range of applications in gene therapy.

Different attempts at constructing retroviral vectors from lentiviruses have been reported. In this respect, the work of Poznansky M. et al (J. Virol 1991, 65, 532-6), Naldini et al (Science, 1996, 272, p 263-7) carried out using the HIV retrovirus and the work of Poeschla E M et al (Nature Medicine, 1998, 4, p 354-7) carried out using the FIV retrovirus can be cited.

The inventors have searched the determinants involved in the mechanism of entry of the retrovirus genome into infected cell nuclei (nuclear import mechanism).

The identification of a triplex DNA determinant essential for import has led the inventors to define novel means, and in particular vectors, for use in transferring genes, or more generally sequences of nucleotides (henceforth termed "transgenes"), into target cells. In particular, the inventors have worked from the HIV (human immunodeficiency virus) retrovirus, a member of the lentivirus family, and have identified and isolated a viral determinant responsible for the nuclear import of proviral DNA of HIV into target cells: central triplex DNA. This DNA triplex has been shown to be able to function in vectors out of the natural context of the HIV-1 genome, as a nuclear import determinant enabling the vector genome to enter the nucleus of target cells.

Mechanisms for retroviral DNA entry into the nucleus exhibit considerable differences from one retroviral family to another. The lentivirus genome is capable of crossing the nuclear membrane of the interphasic nucleus by addressing followed by translocation of its pre-integration complex (linear DNA and associated proteins) through the nuclear pore. Thus such viruses are capable of replicating in the absence of division of the target cell. In particular, they infect differentiated tissue macrophages and dendritic cells, cells at the core of the transmission, dissemination, and the physiopathology of HIV. In contrast, oncovirus genomes and spumavirus genomes are incapable of crossing the barrier constituted by the nuclear membrane. Their pre-integration complex must await mitosis and disorganisation of the nuclear membrane in order to accede to the mitotic chromosomes and be integrated.

The viral determinants responsible for nuclear import of the DNA of the HIV-1 virus have been studied by the inventors. The identification and functional comprehension of the molecular mechanisms of nuclear import of the HIV pre-integration complex is of fundamental importance. The inventors have identified an original mechanism for nuclear import of the HIV-1 genome by which this import is governed by a DNA structure, a triplex at the centre of linear DNA molecules, generated by steps particular to lentiviral reverse transcription.

The triplex DNA structure present at the centre of linear DNA molecules generated during lentiviral reverse transcription, in particular in the HIV retrovirus, has been described by the inventors in different prior publications (Charneau P. et al., J. Mol. Biol. 1994, 241, 651-662; Charneau P et al., Journal of Virology, May 1991, p 2415-2421; Charneau P. et al., Journal of Virology, 1992, vol. 66, p 2814-2820).

Figure 1A:
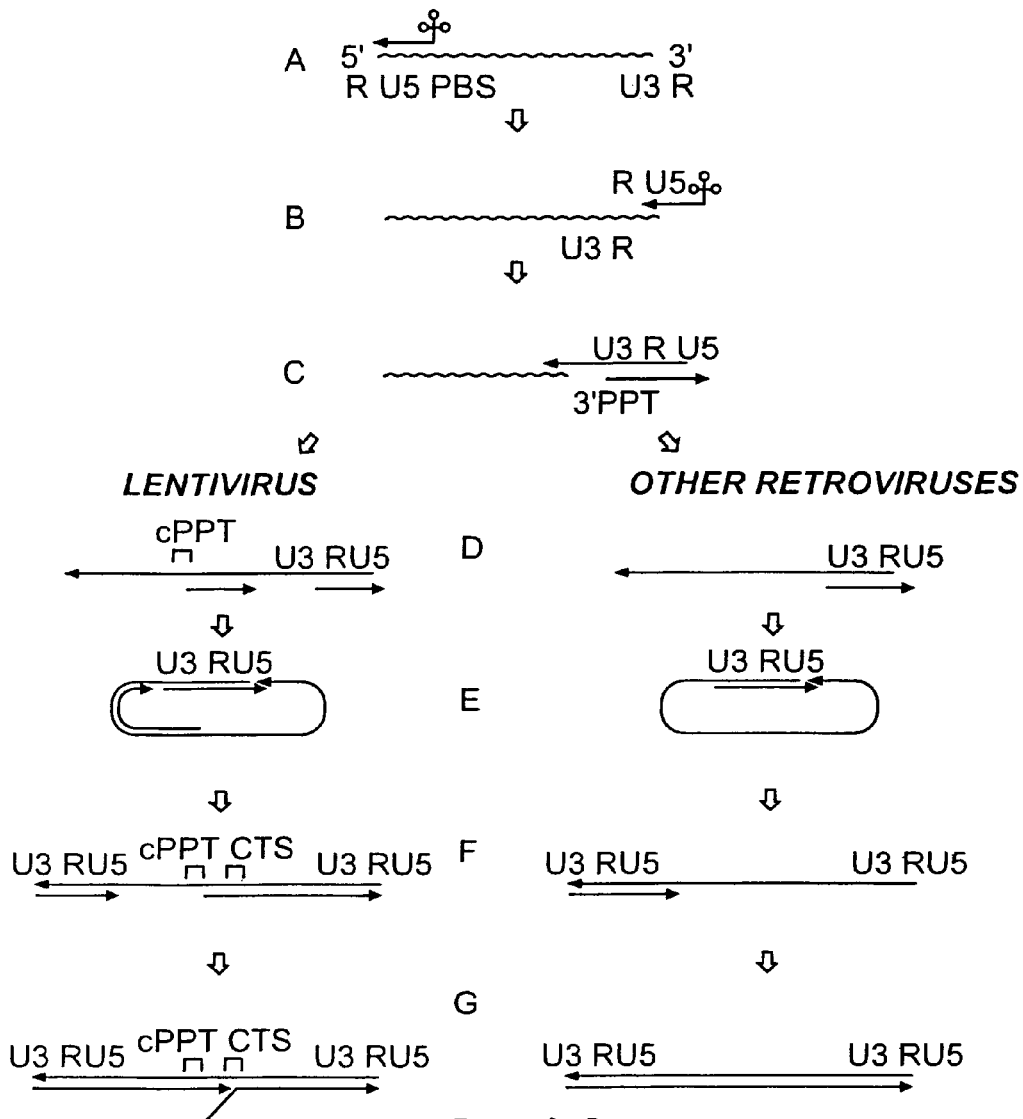
Figure 1B:
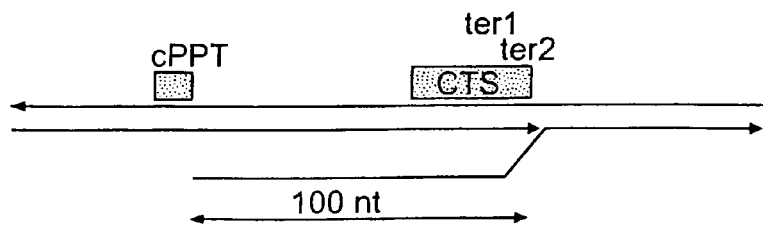

The DNA structure forming a triplex during viral reverse transcription is a polynucleotide comprising a cis-acting central initiation region, or polypurine tract (cPPT), and a cis-acting termination region (CTS), these regions enabling initiation of transcription of a +strand the synthesis of which is initiated by the PPT region present in the centre of the HIV genome or other lentiviruses, and interruption of synthesis of a second +strand the synthesis of which is initiated at a 3' PPT site upstream of the retroviral LTR (FIG. 1).

Formation of the triplex DNA structure is the consequence of a discrete strand displacement event in the retrovirus genome, blocked by the CTS sequence (Charneau P. et al., J. Mol. Biol., 1994). It should be understood that the term "triplex DNA" used here designates a triple-stranded region of DNA, with no reference to the structure of those strands (free displaced strand, or forming a triple helix or a D-loop, etc . . . ).

The structure of the DNA triplex formed during reverse transcription enables or at least contributes to the entry of the retroviral genome into the cell nucleus, thus allowing infection of non mitotic cells.

Starting from the identification of this required mechanism for entry of the retrovirus into the nucleus of target cells, the inventors have produced a novel generation of lentiviral vector, including the triplex DNA region. The introduction of a DNA fragment from the HIV-1 genome comprising the cPPT and CTS sequences which are cis-acting into an HIV vector system increases transduction of genes into the cells by stimulating the amount of nuclear import of the vector DNA. This generation of lentiviral triplex vectors considerably improves transduction of the gene into the cells whether or not they are mitotic.

The invention concerns a nucleotide sequence of retroviral or retroviral-like origin, which can be prepared synthetically, comprising cPPT and CTS regions which are cis-acting in reverse transcription in general, and in particular two associated polynucleotides when they are placed in the normal retroviral genome, each polynucleotide containing at least 10 nucleotides.

The nucleotide sequence of the invention (see FIG. 11G where the cis-acting sequences of interest are boxed) comprises on one side, a short nucleotide sequence termed "cPPT" in the case of HIV-1 (minimum 10 base pairs) and on the other side, a sequence termed "CTS" of at least 10 base pairs in the case of HIV-1. The two cis-acting sequences and a nucleotide sequence from a retroviral genome located between these two cis sequences correspond to about 120 nucleotides in the case of the natural HIV-1 genome.

The invention also concerns a nucleotide sequence comprising three DNA strands constituted by, on one hand, the CTS region (or an equivalent region in the case where the origin of the genome used is other than HIV-1 but with the same properties as the CTS region published by Charneau et al., J. Mol. Biol., 1994) and, on the other hand, upstream of the CTS, a region containing about 90 to 110 nucleotides, preferably 99 nucleotides in the case of HIV-1.

The invention concerns a polynucleotide comprising a double stranded DNA fragment corresponding to the cPPT (polypurine tract) region associated with a polynucleotide sequence naturally present in the HIV-1 genome (or an equivalent natural or synthetic sequence), and finally a CTS nucleotide region which adopts a conformation which defines the end of the triple stranded region (3' end) after reverse transcription.

This triple-stranded conformation is termed a "triplex sequence".

By way of example, the triplex sequence is that shown in FIG. 11F for HIV-1 or FIG. 11G. In vivo, when present in a vector for use for penetrating the nuclear membranes of eukaryotic cells, the triplex stimulates import of DNA into the nucleus of the cell to be modified or transduced.

The invention concerns the use of this triplex sequence alone or in a vector to introduce nucleotide sequences to which the triplex sequence is bound into the nucleus of the receiving eukaryotic cell.

Thus the invention provides a recombinant vector, characterized in that it comprises a polynucleotide containing a cis-acting central initiation region (cPPT) and a cis-acting termination region (CTS), these regions being of retroviral or retroviral-like origin, said vector further comprising a defined sequence of nucleotides (transgene or the sequence of interest) and regulatory signals for reverse transcription, expression and packaging of retroviral or retroviral-like origin.

The term "polynucleotide" used here refers to any nucleic acid sequence in the form of a single or double or triple strand, whether DNA, for example cDNA, or RNA.

By way of example, the invention concerns the transfer of transgenes for therapeutic purposes, in particular within the context of somatic gene therapy protocols, to insert a nucleotide sequence which modulates or repairs a defective activity in the somatic cells of an organism to rectify poor function of an endogenous gene, or to enable expression of a supplementary function, in particular a function which suppresses the expression or the activity of a gene, for therapeutic purposes.

The expression "therapeutic" as used here means the search for or production of a preventative or curative effect, or the search for or production of an improvement or stabilisation of the pathological state of a patient.

Within the context of the invention, and by way of example, the nucleotide sequences termed transgenes or nucleotide sequences of interest can be genes or gene portions or sequences derived from genes, for example cDNA or RNA. They may also be antisense sequences, negative mutant sequences of a given gene, or sequences involved in the functions of gene transcription, expression or activation, or sequences suitable for activation of prodrugs or cytotoxic substances.

The activity of the transgene sequences of the invention can also be to stimulate or induce an immune, cellular or humoral response, for example when used to transform cells presenting an antigen.

Thus the invention can be applied to the preparation of vectors used for gene therapy in various domains such as that of hereditary diseases comprising altering a gene, these diseases including Duchenne's muscular dystrophy, cystic fibrosis, neurodegenerative diseases or acquired diseases such as malignant diseases naturally leading to a weak response of the immune system. The invention can also envisage immunotherapy treatments to stimulate the response to pathogenic agents, for example by the production of CTL, for example in the case of diseases such as cancers or diseases such as AIDS, or to reduce the response against self antigens in the case of autoimmune diseases.

The invention also concerns the provision of means for producing immunogenic compositions or prophylactic or therapeutic vaccines, or immunogenic compositions.

Lentiviral vectors containing a DNA triplex of the invention are also used to construct transgenic animals by transduction of genes into cell lines or embryonic cells.

The vector of the invention contains a transgene inserted under the control of viral or non viral sequences regulating transcription or expression.

The transgene can be included in an expression cassette comprising suitable sequences for regulating its expression in the cell.

A first particularly interesting embodiment of the invention is that in which the recombinant vector is characterized in that the sequences of retroviral origin it contains are derived from the genome of a lentivirus.

Within the context of the present application, the term "derivative" encompasses any sequence identical to the sequence contained in the genome of the retrovirus, or any sequence modified by mutation, insertion, deletion or recombination, provided that it preserves the essential function it possesses in the retroviral genome, with regard to its insertion into the vector of the invention.

Such a sequence could be obtained by any known means enabling identification and isolation of sequences of nucleotides from their organism of origin, in particular comprising the steps of cloning and/or amplification, or by synthesis using any known technique.

Alternatively, the vector of the invention is characterized in that the sequences of retroviral-like origin are derived from a retrotransposon. The retrotransposon yeast TY1 can be mentioned in this regard (Heyman T et al).

The recombinant vector thus described can, for example, be a plasmid recombined by a retroviral or retroviral-like construction and a transgene, if necessary contained in an expression cassette.

The recombinant vector can also be a retrotransposon, a phage, such as a λ phage or a filamentous phage which can be introduced into bacteria, or a vector capable of transforming yeasts such as a YAC.

Such a vector can be used for cell transduction, and in particular packaging of cells and/or target cells, by any method which is known per se, including transfection or infection or transduction, for example by an adenovirus or AAV type vector containing the triplex lentiviral vector.

A vector as defined above can be transcomplemented by one or more additional vectors carrying sequences coding for structure polypeptides from the genome of a selected retrovirus, in particular a lentivirus, or structure polypeptides of a retrotransposon.

In this regard, the vector of the invention can be transcomplemented by providing sequences coding for the polypeptides GAG, POL and ENV, or for a portion of these polypeptides sufficient to enable formation of retroviral particles aimed to vectorise the recombinant vector deprived of viral genes and comprising the transgene the expression of which is sought.

A vector of the invention can be characterized in that the transgene or sequence of interest is contained in an expression cassette comprising signals regulating transcription and expression.

In general, the vector(s) used for transcomplementation into retroviral or retroviral-like proteins are depleted in packaging signals.

In this regard, the vectors prepared using the techniques of Goldman et al (1997) for use in transcomplementation of a recombinant vector of the invention can be cited.

The invention also concerns recombinant retroviral vector particles comprising:

a) a gag polypeptide corresponding to nucleproteins of a lentivirus or to functional polypeptide derivatives (GAG_polypeptides);

b) a pol polypeptide constituted by the proteins RT, PRO, IN of a lentivirus or a functional polypeptide derivative (POL polypeptide);

c) an envelope polypeptide or functional polypeptide derivatives (ENV polypeptides);

d) a recombinant nucleotide sequence comprising a defined nucleotide sequence (transgene or a sequence of interest) placed under the control of regulatory signals for transcription and expression, a sequence containing regulatory signals for reverse transcription, expression and packaging of retroviral or retroviral-like origin and a polynucleotide comprising a cis-acting central initiation region (cPPT) and a cis-acting termination region (CTS), said regions being of retroviral or retroviral-like origin and being inserted in a functional orientation with said regulatory signals of retroviral or retroviral-like origin.

The invention also concerns recombinant retroviral vector particles comprising:

a) a nucleotide sequence termed a gag sequence coding for nucleoproteins of a lentivirus or for functional polypeptide derivatives (GAG polypeptides);

b) a nucleotide sequence termed a pol sequence coding for the proteins RT, PRO, IN and RN of a lentivirus or for a functional polypeptide derivative (POL_polypeptide);

c) regulatory signals for transcription and expression of the gag and pol sequences;

d) a nucleotide sequence termed an env sequence coding for envelope polypeptides or for functional polypeptide derivatives (ENV polypeptides), the env sequence being placed under the control of regulatory signals for transcription and expression;

e) a recombinant nucleotide sequence comprising a defined sequence of nucleotides (transgene), placed under the control of regulatory signals for transcription and expression, a sequence containing regulatory signals for reverse transcription, expression and packaging of retroviral or retroviral-like origin, and a polynucleotide comprising a cis-acting central initiation region (cPPT) and a cis-acting termination region (CTS), said regions being of retroviral or retroviral-like origin, said regions being inserted in a functional orientation with regulatory signals of retroviral or retroviral-like origin.

In one variation, the invention provides a nucleotide sequence comprising a polynucleotide comprising a cis-acting central initiation region (cPPT) and a cis-acting termination region (CTS), of retroviral or retroviral-like origin, each of said two regions flanking a concatenation of internal nucleotides, said cis-acting cPPT and CTS regions being inserted into said nucleotide sequence, in a functional orientation with regulatory signals for reverse transcription of retroviral or retroviral-like origin.

GAG_and POL_polypeptides are nucleoprotein polypeptides from precursors cleaved by viral protease. POL_polypeptides comprise reverse transcriptase (RT), protease (PRO), integrase (IN) and Rnase H (RN) of the retrovirus. If necessary, other retroviral proteins are also used to construct vector particles. It should be noted that the terms "proteins" or "polypeptides" used here encompass the non glycosylated forms or the glycosylated forms of the polypeptides in question.

The gag, pol and env sequences used to construct retroviral vector particles can, if necessary, be modified by mutation, for example by point mutation or by deletion or insertion of one or more nucleotides, or may originate from recombinant chimeras originating from different retroviruses, for example HIV-1 and HIV-2 or HIV-1 and CAEV (Caprine Arthritis Encephalitis Virus), provided that they allow the production of functional polypeptides for the production of viral particles capable of vectorising the transgene to be expressed. In particular, mutated sequences are used to increase the safety of the retrovirus produced.

Advantageously, the recombinant vector of the invention or recombinant vector particles are such that the transgene is under the control of regulatory signals for transcription and expression of non retroviral origin. An example of a promoter which can be used to control expression of the transgene is the CMV promoter, the PGK promoter or EF1α promoter described by Tripathy, S K et al (PNAS 1994, 91, p 11557-11561).

In a variation of the invention, the transgene can be placed under the control of regulating signals previously identified as being retroviral or retroviral-like in origin, in particular under the control of the LTR sequence.

A lentivirus used to derive the retroviral construction of the invention can be selected from the HIV retrovirus, for example HIV-1, HIV-2 or any different isolate of these two types, or for example from the CAEV (Caprine Arthritis Encephalitis Virus) virus, EIAV (Equine Infectious Anaemia Virus), VISNA, SIV (Simian Immunodeficiency Virus) or FIV (Feline Immunodeficiency Virus).

A particularly advantageous vector of the invention is a vector characterized in that the polynucleotide is a DNA sequence comprising the cis-acting central initiation region (cPPT) and the termination region (CTS) of the genome of an HV1 retrovirus or any other lentivirus.

The central PPT sequence or cPPT sequence is a relatively conserved sequence in lentiviruses and is identified by the presence of numerous purine residues certain of which are shown in FIG. 11H. Mutations, even point mutations in one of these regions, can destroy the functional nature linked to the formation of DNA triplex structures.

The identification of cPPT sequences is facilitated by the fact that a polypurine sequence located at the upstream edge (5') of the 3' LTR in all retroviruses is repeated in the centre of the genome in lentiviruses. This cPPT sequence can be an exact repeat as in the HIV-1 virus, or slightly modified in other lentivirus (FIG. 11H). The central termination sequence CTS has been characterized for the HIV-1 virus (Charneau et al, 1994). It is located about one hundred nucleotides downstream of the cPPT sequence. In other lentiviruses, CTS sequence candidates are also about a hundred nucleotides (80 to 120 nucleotides) downstream of the cPPT sequence. The probable position of the CTS sequence is indicated for several lentiviruses in FIGS. 11A to 11E.

The CTS sequence of the EIAV lentivirus has recently been characterized (Scott R. Stetor et al Biochemistry 1999, 38, p 3656-67). According to the authors, in EIAV, the cPPT and CTS sequences are respectively

```
5'AAC AAA GGG AGG GA 3'  (SEQ ID NO: 1)
and

5' AAA AAA TTT TGT TTT TAC AAA ATC 3' (SEQ ID NO:
2).
```

Examples of preferred polynucleotides for use in the invention which can be cited are the sequences shown in FIG. 11, more precisely the sequences between the two regions cPPT and CTS, including the sequences in those regions.

If necessary, the sequence of nucleotides comprising cPPT, the internal polynucleotide (i.e., binding the cPPT to the CTS sequence) and the CTS sequence can be point mutated or mutated by deleting or inserting nucleotides. By way of example, point mutations have been produced in the cPPT sequence of HIV-1 and have shown that it retained residual infectivity in the cells (Charneau et al, J. Virol. 1992, 66, p 2814-2820).

The invention encompasses any mutated sequence for cPPT or CTS which is at least 60% identical to the natural homologous cis-acting nucleotide sequence from which it originates. In the case of chimera cis-acting sequences, the percentage is applied to each mutated nucleotide sequence of the chimera.

Modifications to the nucleotide sequence of the PPT or cPPT or CTS regions can be introduced to construct the triplex DNA of the invention. Such modifications can reach up to 40% of the natural sequence.

The identity of the nucleotide sequences which vary with respect to the natural sequences is calculated strictly with respect to the cPPT or CTS individually and not with respect to the complete triplex DNA nucleotide sequence.

The region between the cPPT and CTS is constituted by a polynucleotide which can either be that found in the original retroviral genome between the CTS and PPT or it can be different therefrom provided that the triplex DNA retains its properties as regards nuclear import of the polynucleotide to enable the nucleotide sequence of interest to be taken inside the nucleus.

The polynucleotide of the invention can be introduced into a replicative or non replicative vector. In the case of a retroviral vector, it is a non replicative vector.

In order to prepare large quantities of retroviral vector particles, it is possible to use adenoviral type vectors into which the polynucleotide corresponding to the retroviral genome which contains the triplex DNA sequences and those of the gag, pol and env genes has been introduced.

These adenoviral vectors can optionally be rendered replicative by introducing an origin of replication sequence.

FIG. 11G shows the cPPT and CTS sequences of HIV-1 in boxes.

In all cases, mutated sequences will be used which retain the capacity to form a DNA triplex during reverse transcription of the genome in the target cell.

A recombinant vector in accordance with a particular implementation of the invention can thus comprise all or a portion of the retroviral or retrotransposon LTR sequences, retroviral PBS sites, and 3'-terminal PPT, the retroviral sequence necessary for packaging of the vector genome in the vector particle. The LTR sequence can be partially deleted, in particular in the U3 region.

Figure 10:
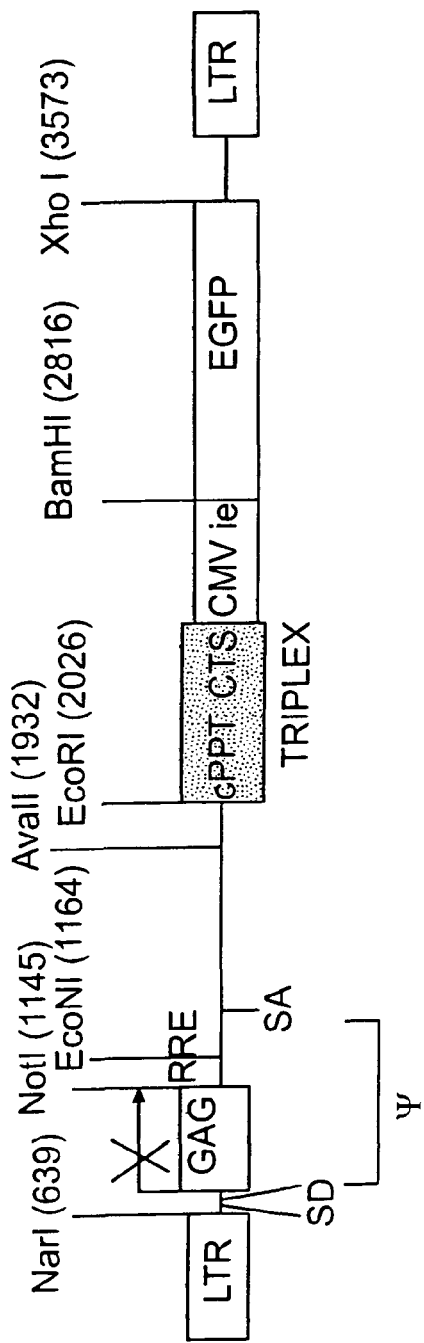

A particular vector of the invention is the plasmid pTRIP.EGFP which has been deposited at the CNCM (Collection National de Cultures de Microorganismes [National Micro-organism Culture Collection] by the Institut Pasteur, France) on 15 Apr. 1998, accession number I-2005. The restriction map for this vector is shown in FIG. 10.

Another vector in accordance with the invention is the plasmid pTRIP.MEL-IRES-GFP deposited at the CNCM on 20 Apr. 1999, accession number I-2185. This vector is the plasmid pTRIP.MEL-IRES-GFP shown in FIG. 14.

A particular recombinant vector of the invention is characterized in that the gag, pol and env sequences are also derived from lentivirus sequences, in particular an HIV retrovirus, more particularly HIV-1 or HIV-2.

In a further implementation of the invention, the gag and pol sequences are derived from an HIV retrovirus and the env sequence is derived from a retrovirus which is distinct from HIV or from a virus, for example the vesicular somatitis virus (VSV).

In general, and as a function of the expression of the transgene which is being researched, an env sequence coding for env polypeptides which are amphotropic with respect to the host in which the transgene is to be expressed can be selected, or env sequences coding for ecotropic env polypeptides can be selected. The tropism of the env sequence can be a specifically human tropism.

The invention also provides recombinant vector particles comprising a recombinant sequence of nucleotides comprising a defined nucleotide sequence (transgene or sequence of interest) placed under the control of regulatory signals for transcription and expression, regulatory signals for reverse transcription and expression, a sequence containing regulatory signals for expression and packaging and a polynucleotide comprising a cis-acting central initiation region (cPPT) and a cis-acting terminal region (CTS).

The invention also provides recombinant vector particles comprising a sequence of recombinant nucleotides comprising a defined nucleotide sequence (transgene) placed under the control of regulatory signals for transcription and expression, regulatory signals for reverse transcription, expression and packaging of a retrotransposon and a polynucleotide comprising a cis-acting central initiation region (cPPT) and a cis-acting terminal region (CTS), these regions being derived from a retrotransposon and inserted in a functional orientation with retrotransposon regulatory signals.

Further, the invention also concerns recombinant vector particles comprising:

a) a GAG polypeptide corresponding to the nucleoproteins of a retrotransposon or to functional polypeptide derivatives;

b) a POL_polypeptide corresponding to the RT, PRO, IN proteins of a retrotransposon or to a functional polypeptide derivative;

c) regulatory signals for transcription and expression of gag and pol sequences;

d) a recombinant nucleotide sequence comprising a defined nucleotide sequence (transgene) placed under the control of regulatory signals for reverse transcription, expression and packaging of a retrotransposon and a polynucleotide comprising a cis-acting central initiation region (cPPT) and a cis-acting terminal region (CTS), said regions being derived from a retrotransposon and inserted in a functional orientation with retrotransposon signal regulators.

Further, the invention concerns recombinant vector particles resulting from expression of:

a) a nucleotide sequence termed a gag sequence coding for nucleoproteins of a retrotransposon or for functional polypeptide derivatives (GAGpolypeptides);

b) a nucleotide sequence termed a pol sequence coding for the RT, PRO and IN proteins of a retrotransposon or for a functional polypeptide derivative (POL polypeptide);

c) regulatory signals for transcription and expression of gag and pol sequences, said particles comprising a recombinant sequence of nucleotides comprising a defined sequence of nucleotides (transgene) placed under the control of regulatory signals for transcription and expression, a sequence containing regulatory signals for reverse transcription, expression and packaging of a retrotransposon and a polynucleotide comprising a cis-acting central initiation region (cPPT) and a cis-acting termination region (CTS), these regions being derived from a retrotransposon and inserted in a functional orientation with retrotransposon signal regulators.

The invention further concerns recombinant retroviral-like particles comprising:

a) a polynucleotide comprising a cis-acting central initiation region (cPPT) and a cis-acting termination region (CTS), said regions being derived from a retrotransposon and inserted in a functional orientation with retrotransposon signal regulators;

b) a polypeptide corresponding to nucleoproteins of a retrotransposon or to functional polypeptide derivatives (GAG-polypeptides);

c) a pol polypeptide corresponding to the RT, PRO, IN proteins of a retrotransposon or to a functional polypeptide derivative (POL_polypeptide);

d) a viral envelope polypeptide;

e) a recombinant nucleotide sequence comprising a defined sequence of nucleotides (transgene or sequence of interest) placed under the control of regulatory signals for transcription and expression, regulatory signals for reverse transcription, expression and packaging of a retrotransposon.

As an example, the invention concerns a recombinant vector as defined above, in which the regulatory signals for reverse transcription, expression and packaging and the polynucleotide comprising the cPPT and CTS regions are derived from a retrotransposon, for example a yeast retrotransposon.

In general, the signals regulating transcription and expression of the transgene or sequences coding for structure polypeptides of the vector particle, when they are not retroviral or retroviral-like in origin, are advantageously inducible or conditional signals which are capable of leading to tissue-specific expression.

Recombinant cells characterized in that they are recombined with a vector according to any one of the above definitions are also encompassed by the invention. Recombination can be carried out using any suitable means, in particular transfection or infection, especially transfection or transduction by a vector.

The cells can thus be transiently or stably transfected. They may be packaging cells or target cells, in particular cells in which a therapeutic effect is sought by expression of the transgene.

Particularly interestingly, recombinant cells which are capable of expressing the transgene due to transduction using a vector of the invention are non mitotic differentiated eukaryotic cells.

The invention also encompasses the preparation of recombinant non mitotic primary eukaryotic cells, or mitotic cells.

Examples which can be cited are the cells of the lung; brain, epithelial cells, astrocytes, microglia, oligodendrocytes and neurons, muscle cells, hepatic cells, dendritic cells, neuron cells, bone marrow cells, macrophages, fibroblasts, lymphocytes and haematopoietic cells.

Thus the invention relates to compositions with a therapeutic purpose, characterized in that they comprise a vector as described above, or a recombinant cell defined as indicated above.

The invention also concerns an immunogenic composition comprising a vector as described above or recombinant cells as defined above, said composition being capable of leading to an immune, cellular or humoral response in a given host.

The invention thus provides a polynucleotide as defined above comprising retroviral or retroviral-like cPPT and CTS regions which provides access to its use for nuclear import of a nucleotide sequence (transgene), in particular ex vivo in defined cells.

Further, the invention provides a polynucleotide as defined above associated with a nucleotide sequence of interest or with a transgene.

Finally, the invention concerns the use of a polynucleotide comprising a cis-acting central initiation region and a cis-acting termination region (CTS), these regions being retroviral or retroviral-like in origin, for transfection or transduction of eukaryotic cells with a transgene or polynucleotide of interest.

It also concerns the use of a recombinant vector or a polynucleotide of the invention for in vivo transduction.

Further characteristics and advantages of the invention will become apparent from the following examples and figures.

LEGEND TO FIGURES

FIG 1: Reverse Transcription of Lentivirus

Reverse transcription of lentiviral genomes differs from that of oncogenic retroviruses by the synthesis of the +strand in two distinct halves. A downstream segment is initiated at a central copy of the polypurine tract (cPPT) characteristic of lentiviral genomes. Synthesis of the upstream +strand is terminated after displacement of the discrete strand at the centre of the genome. Blocking of displacement of the strand by reverse transcriptase is governed by a cis-acting sequence of the HIV genome: the CTS (central termination sequence). The final product of reverse transcription of the lentivirus is a linear DNA carrying a central triple-stranded DNA structure (central triplex) over a length of about one hundred nucleotides.

Figure 2:
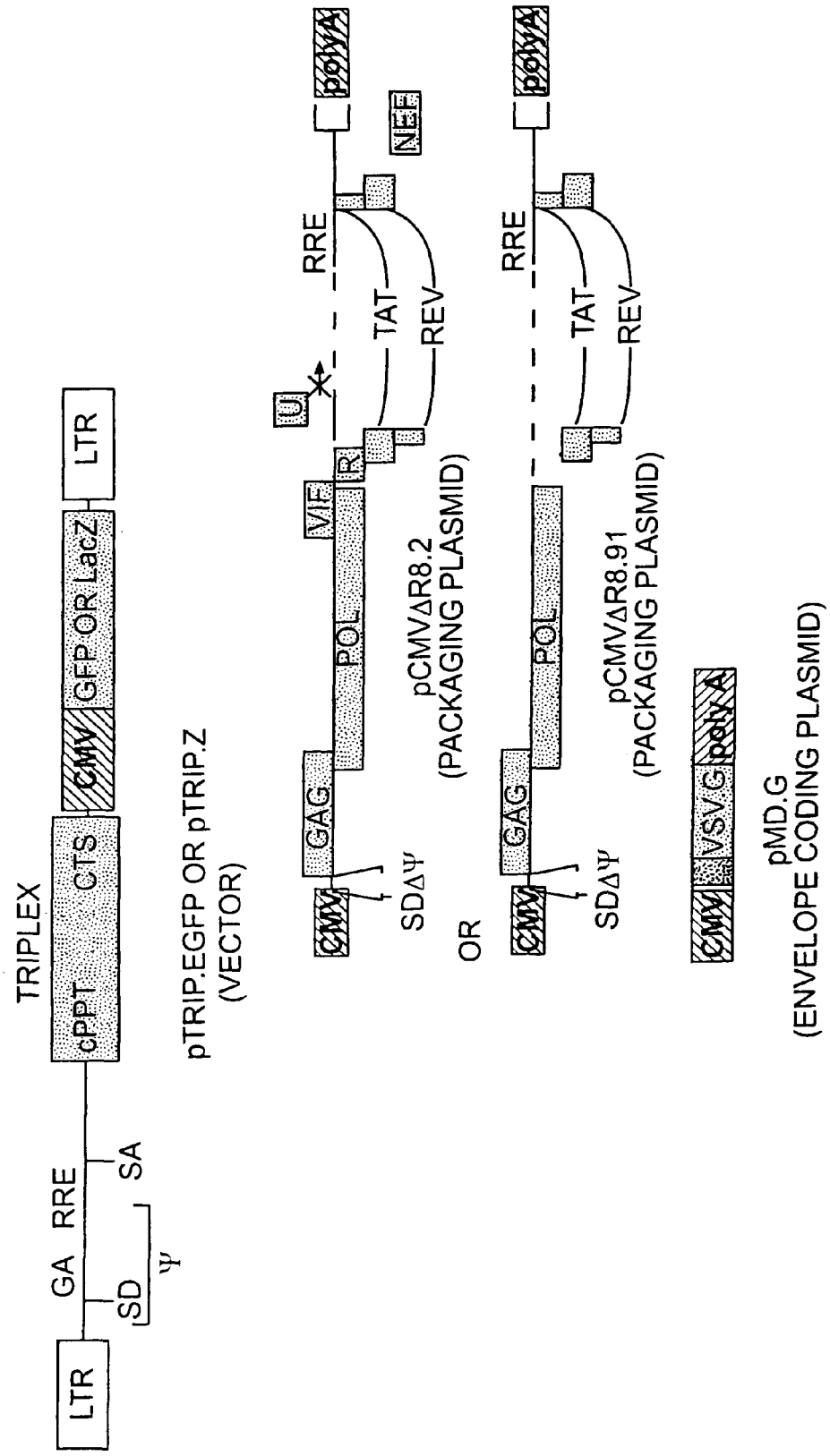

FIG. 2: Plasmids Used for Producing HIV Vector Particles

Vector particles were produced by co-transfection of three plasmids: the vector plasmid comprising (pTRIP) or not comprising (pHR) the cis-acting sequences responsible for triplex formation, a packaging plasmid providing, trans, the structural proteins and enzymes of the particle (pCMVΔR8.2 or pCMVΔR8.91) Naldini et al, 1996 and Zufferey et al, 1997), and a VSV virus envelope expression plasmid (VSV-G).

Only the pertinent parts of the plasmids co-transfected into HeLa cells are shown (Naldini et al PNAS, Oct 1996, Zufferey et al, Nature Biotech, 1997).

The packaging plasmids pCMVΔR8.2 or pCMVΔR8.91 enable expression of the proteins from gag and pol.

PMD.G codes for the heterologous VSV envelope. The vector plasmids pHR-TRIP were derived from the pHR'CMVlacZ plasmid (Naldini et al): a wild type or mutant triplex sequence has been inserted and the lacZ reporter gene, changed or otherwise in EGFP.

FIG. 3: Impact of Triplex on Transduction of EGFP into HeLa Cells

HeLa cells, cultivated in an 8 chamber Labtek, were transduced by different vectors expressing the autofluorescent protein EGFP. The infections were normalised for the quantity of capsid protein (P24 ELISA kit, Dupont) to 2 ng of P24 per inoculum. 48 hours post-infection, the cells were fixed with 1% PBS PFA, mounted in mowiol, then observed with a fluorescence microscope. Three independent fields are shown for the vector of origin with no triplex (HR.EGFP, top), for the vector with triplex (TRIP.EGFP, middle) or for a vector containing a mutated non functional triplex sequence (TRIP D.EGFP, bottom). The right hand side shows the different transductions in the presence of nevirapine, an inhibitor for HIV-1 reverse transcriptase.

Figure 4A:
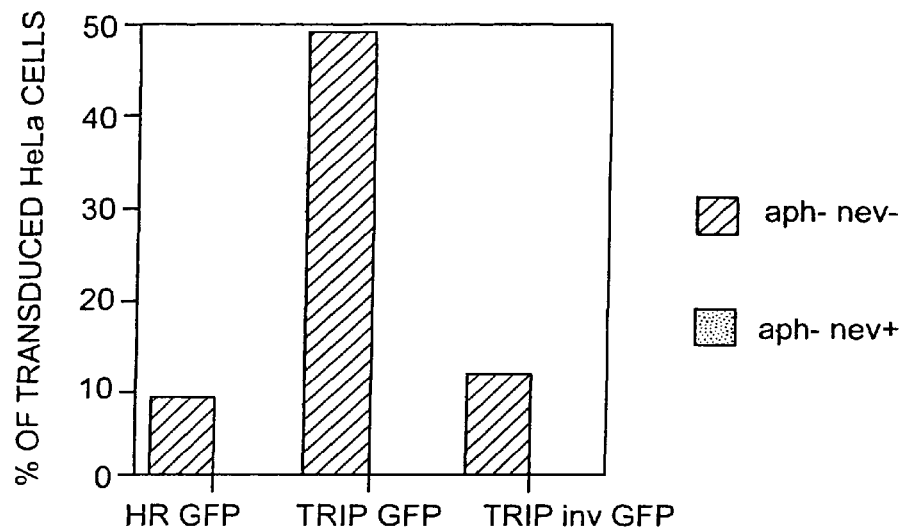
Figure 4B:
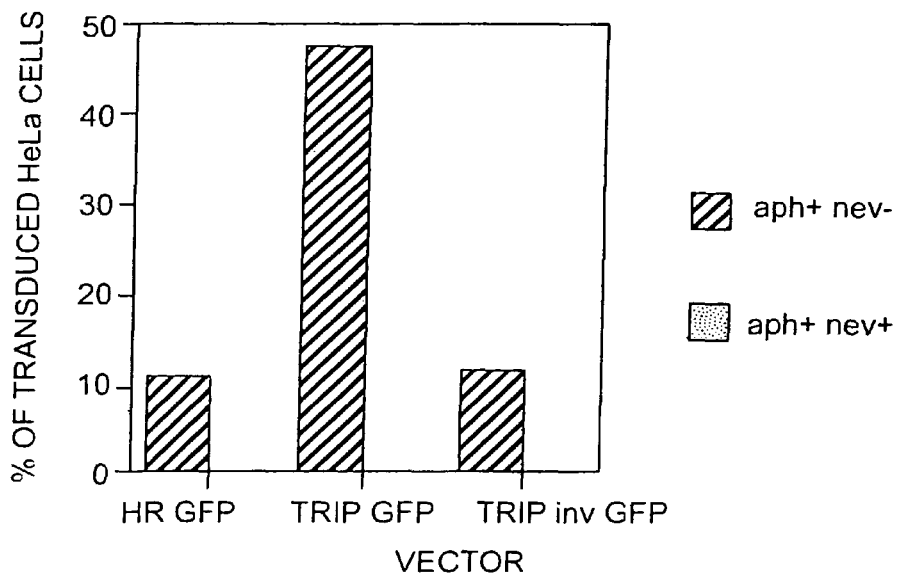
Figure 4C:
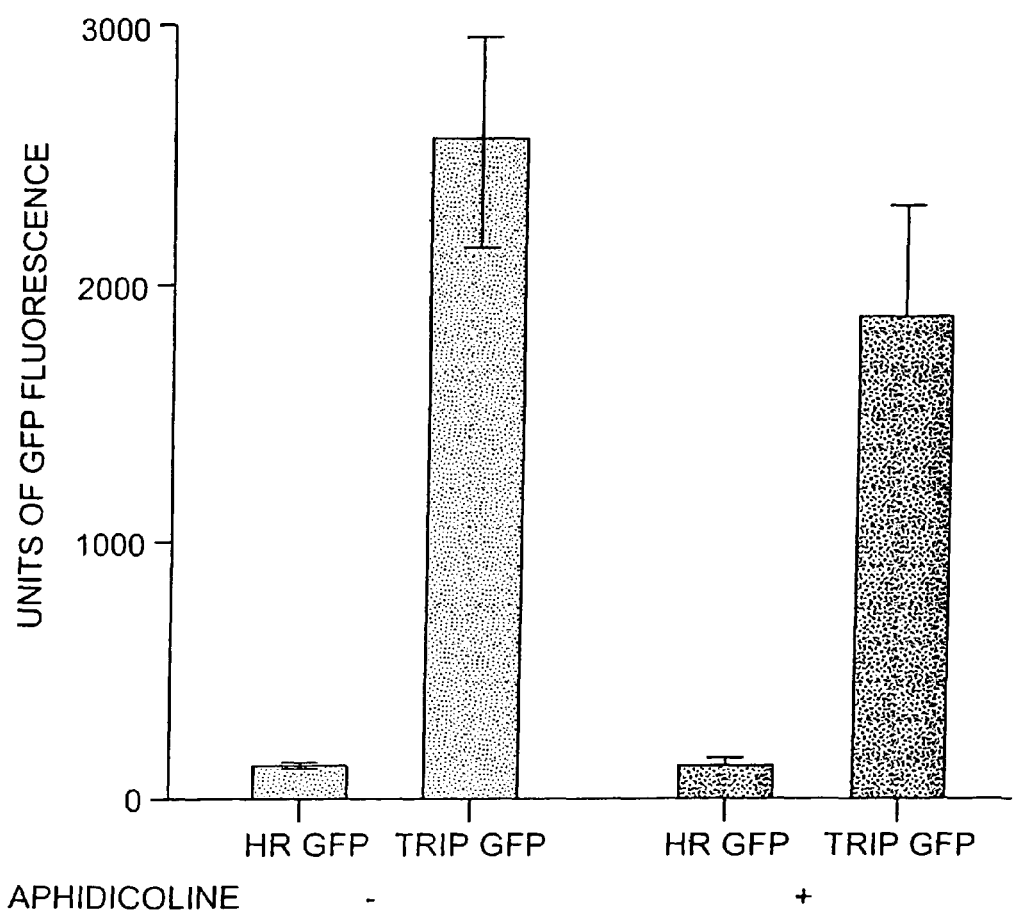

FIG. 4: Quantification of the Degree of Transduction of the EGFP Gene by HIV Vectors with or without Triplex HeLa cells transduced by 2 ng P24 of EGFP vectors with or without triplex were trypsined 48 hours post-infection. The percentages of cells which were positive for EGFP expression were calculated by flow cytometry (FITC channel) for mitotic (FIG. 4A) and blocked (FIG. 4B) HeLa cells. In all cases, transduction was inhibited in the presence of nevirapine, an HIV-1 reverse transcriptase inhibitor. In FIG. 4C, the presence of the triplex DNA was observed in the vector stimulated by transduction of GFP (or another gene of interest) in cells in mitosis or non mitotic cells. This transduction was multiplied by a factor of 20 with respect to the results obtained with vectors without a triplex sequence (for example, see Naldini et al, Science, 1996).

Figure 5A:
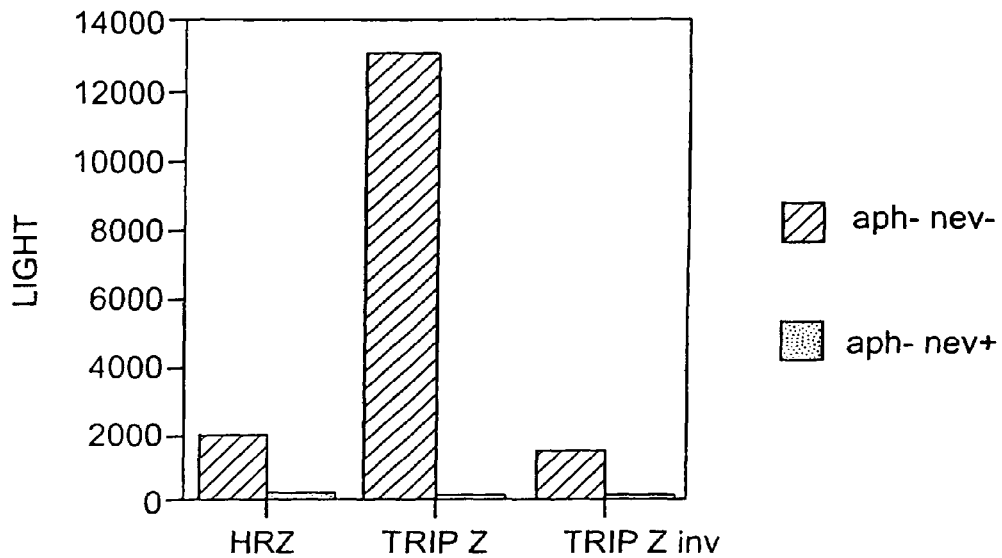
Figure 5B:
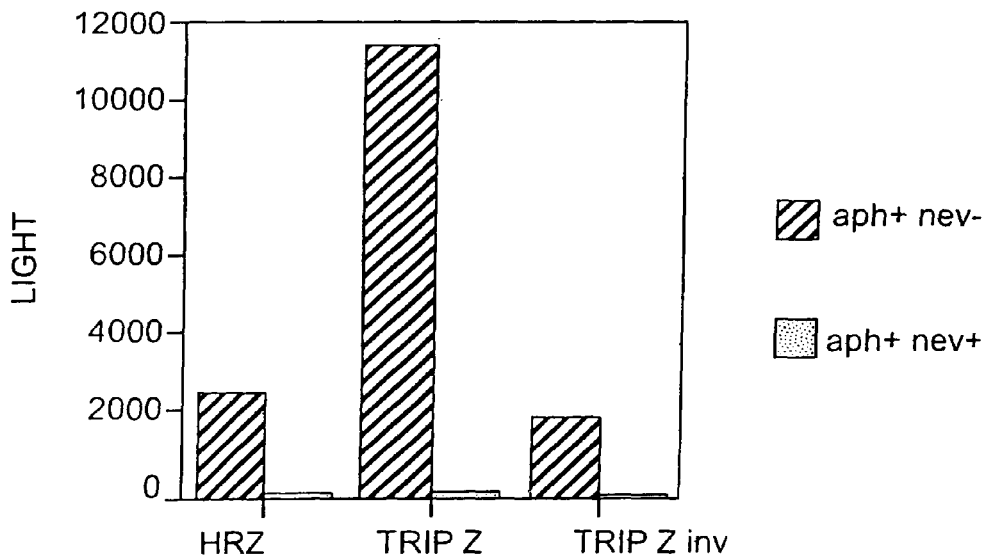

FIG. 5: Quantification of the Degree of Transduction of the LacZ Gene by HIV Vectors with or without Triplex The impact of the triplex on transduction was calculated by infecting HeLa cells, cultivated in 96 well trays, using different vectors expressing the lacZ reporter gene. 48 hours post infection, the culture trays were lysed and the beta-galactosidase activity was measured using a luminescent reaction kit (Boehringer). Each transduction was carried out in triplicate with an innoculum normalised to 2 ng of P24.

Upper panel: proliferating HeLa cells.

Lower panel: HeLa cells blocked in their cycle by aphidicoline.

Transduction of the lacZ gene was multiplied by a factor of 6 with a vector containing a triplex sequence with respect to a vector with no triplex sequence.

Figure 6A:
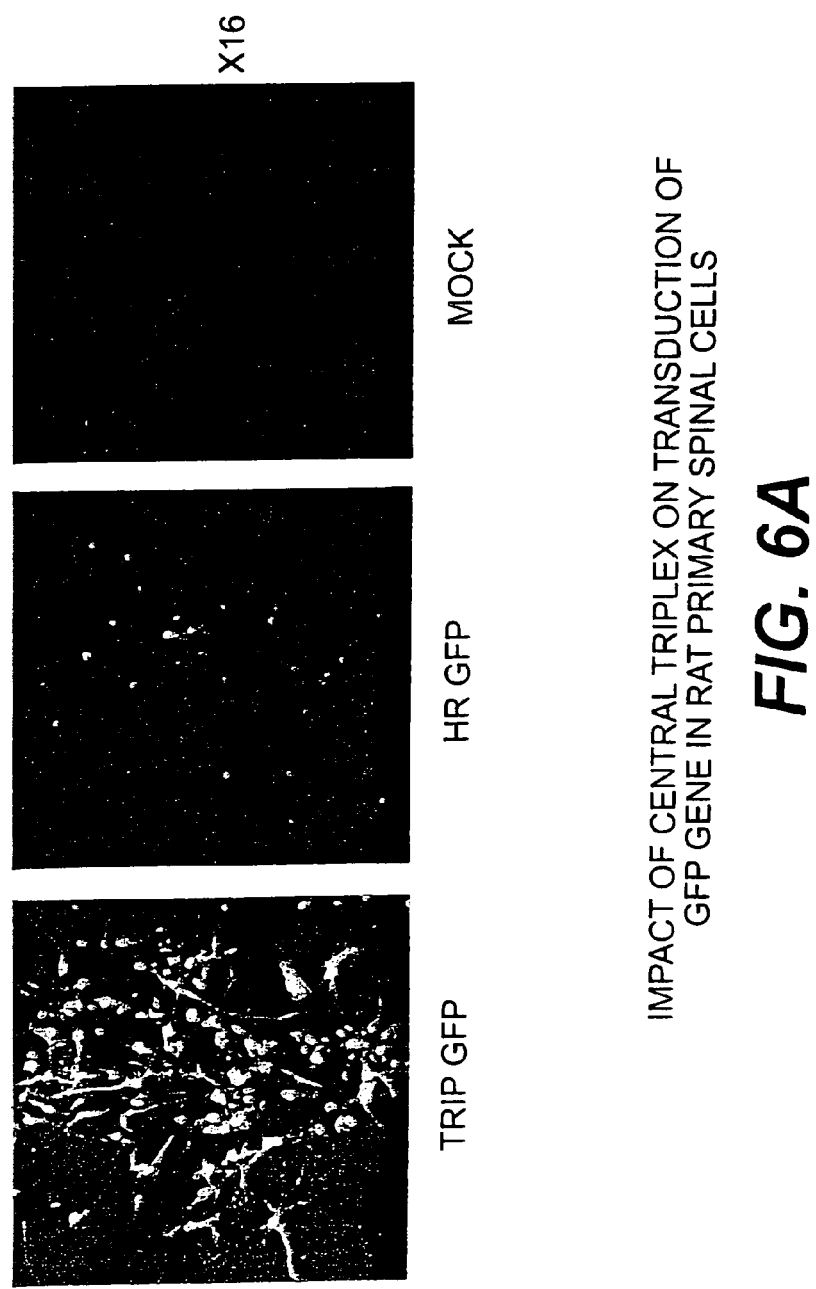

FIGS. 6a & b: Impact of Triplex on Ex Vivo Transduction of the EGFP Gene in Rat Spinal Primary Cells Primary explant cells from rat spinal cord were infected with 300 ng of P24 for each vector with and without triplex, and observed using a fluorescence microscope as described above.

FIG. 7: Impact of Triplex on In Vivo Transduction of EGFP Gene and Luciferase Gene in Rat Brain FIG. 7-a-1: Transduction at injection site.

The EGFP gene was transferred by direct injection into the striatum of the rat brain of 2 microlitres of the vector corresponding to 50 ng of P24.

Observation of the sections under fluorescence microscopy showed a large transduction of EGFP in the presence of triplex (left hand panel) and very little without (right hand panel).

FIG. 7-a-2: Another section representing the experiment described above.

FIG. 7-b: Quantification of impact of triplex on in vivo transduction in the brain.

FIG. 7-b-1: Impact of triplex on transduction of the gene coding for luciferase in in vitro HeLa cells. The graph shows the luciferase production quantified by measuring luminescence (Promega® kit). The presence of the triplex in the vector increased transduction of the luciferase gene by a factor of 8.

FIG. 7-b-2: In vivo quantification of luciferase activity in rat brains after injection of vectors coding for luciferase, with or without triplex. The presence of triplex stimulates luciferase transduction by a factor of 8.

FIG. 7-b-3: Same experiment as 7-b-2 but carried out in the mouse.

FIG. 8: Strategy for analysis of amount of nuclear import of vector DNA.

A quantitative test enabling the reverse transcription, nuclear import and integration or circularisation kinetics of the vector DNA in transduced cells was developed. This test advantageously replaced detection by PCR amplification of circles with two LTRs, markers for nuclear import of viral DNA into the nucleus of the infected cell (Bukrinsky et al, Nature 1993, 365, p 666-669). The non integrated linear vector DNA, circular DNAs with one or two LTRs and integrated vector DNA were detected by Southern blot and quantified using a Phosphorimager using the following restriction digestion strategy: the total DNA of the transduced cells was digested with EcoNI and AvaII (two unique sites in the vector genome) then hybridised with a DNA probe generated by PCR precisely spanning the EcoNI site. This probe reacted with different fragments: the internal 0.77 kb fragment, common to all of the vector DNA forms, and for which quantification using the phosphorimager indicated the total quantity of reverse transcribed vector DNA; a distal fragment of 1.16 Kb specifically indicating the quantity of linear non integrated DNA. After supplemental digestion by the Xho1 enzyme, spots with one or two LTRs appeared at 1.4 Kb and 2 Kb respectively. The quantity of integrated vector DNA was calculated by subtracting the signals corresponding to non integrated vector DNA, linear DNA and spots from the signal corresponding to the total reverse transcribed DNA. In the case of a lack of nuclear import, the expected vector DNA profile in the transduced cells is an accumulation of non integrated linear DNA. In contrast, if the vector DNA reaches the nuclear compartment of the cell, the essential part of the linear DNA is integrated into the cellular chromatin and circularises.

Figure 9A:

FIG. 9a: Analysis of Nuclear Import of Vector DNA

Southern blot analysis 48 hours post transduction in HeLa cells showed a typical lack of nuclear import in the case of the vector without triplex (HR GFP) or containing the triplex sequence in the reverse orientation, which is non functional (TRIP, GFP inv). In the case of these vectors, the signal corresponding to non integrated linear DNA was equivalent to the total DNA signal, indicating that the essential part of the vector DNA remained in the linear form instead of becoming integrated. In the case of the TRIP.GFP vector, the intensity of the signal corresponding to linear DNA was very much lower than the total DNA signal, indicating that a large fraction of vector DNA had been imported into the nucleus and had been integrated therein.

Figure 9B:
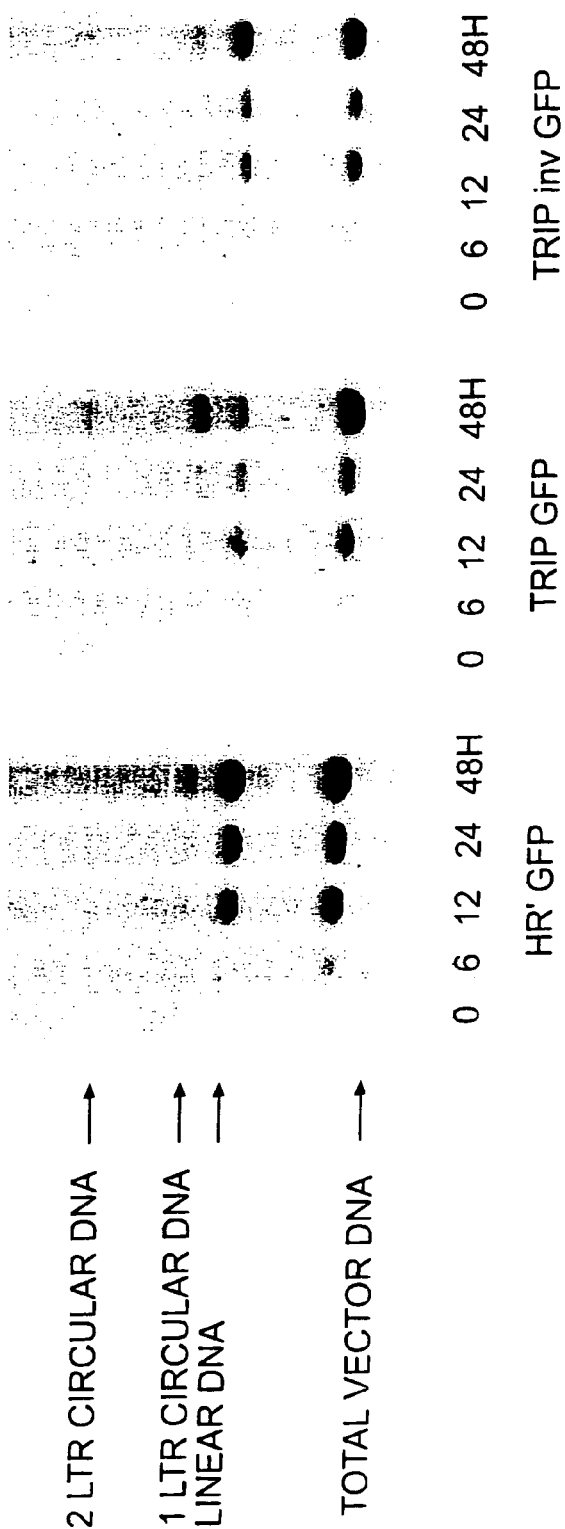
Figure 9C:
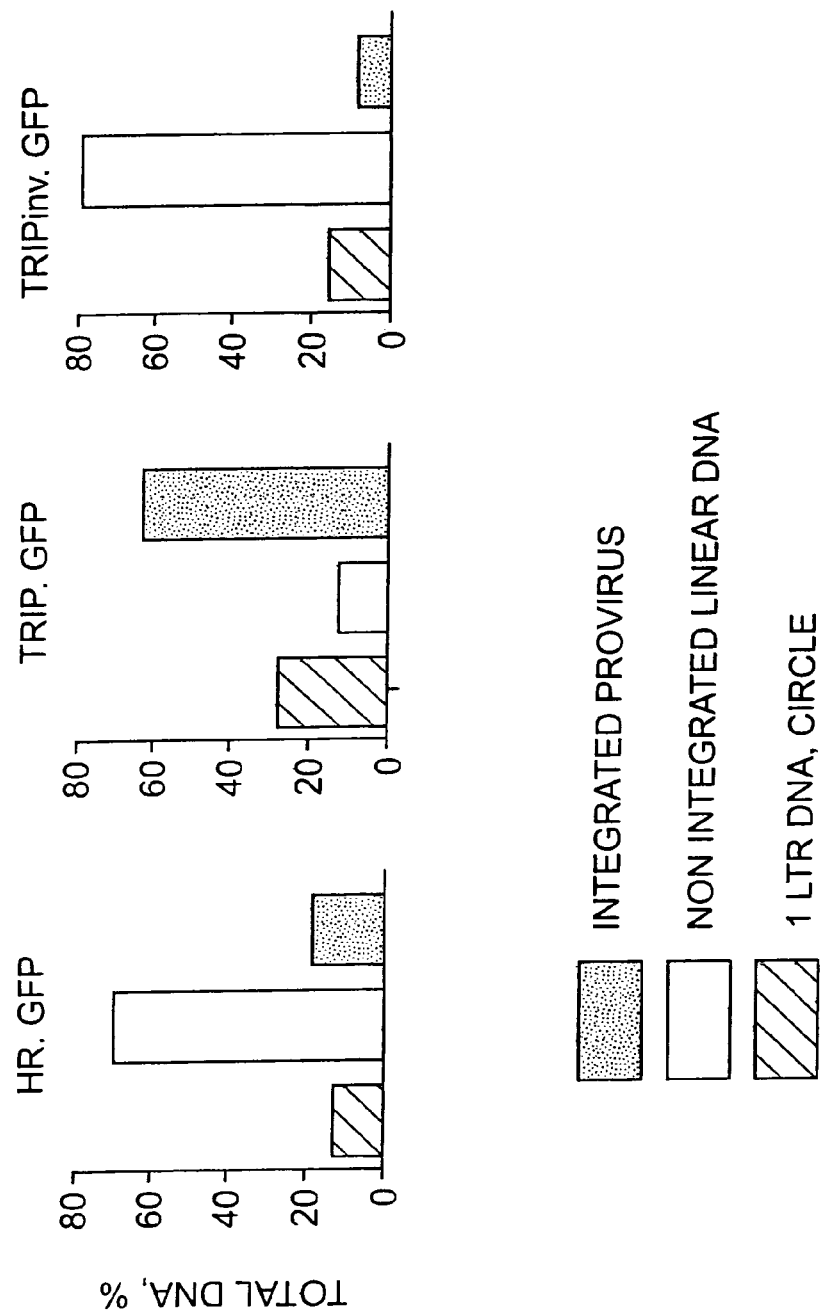

FIG. 9-b: Kinetic analysis of degree of nuclear import of vector DNAs with triplex (TRIP-GFP) or without triplex (HR-GFP, TRIPinv-GFP).

FIG. 9-c: Quantification of state of vector DNA in transduced cells.

Phosphorimager quantification of the Southern blot of FIG. 9b showed that 48 hours post-transduction, the majority of the DNA of the vectors without triplex were in the form of linear non integrated DNA; only a little vector DNA had integrated or circularised. The triplex-free vectors (HR-GFP and TRIPinv-GFP) exhibited a typical lack of nuclear import. In contrast, in the case of the TRIP-GFP vector, more than 60% of the DNA had integrated into the genome of the transduced cell and only a little vector DNA subsisted in the form of non integrated linear DNA. Introduction of the triplex sequence into the vector had complemented the lack of nuclear import of the HR-GFP vector to the level of the wild type. In fact, the vector DNA profile obtained in the case of the TRIP-GFP vector was comparable with that of a wild type HIV-1 virus. This result shows that the triplex sequence is the only determinant of nuclear import lacking in the HR-GFP construction. Only the integrated form of the DNA vector was active.

FIG. 10: Restriction map for pTRIP.EGFP vector.

FIGS. 11A-11F: Polynucleotide sequence comprising cPPT and CTS regions of the CAEV (SEQ ID NO:9), EIAV (SEQ ID NO:10), VISNA (SEQ ID NO:11), $SIV_{AGM}$ (SEQ ID NO:12), $HIV-2_{ROD}$ (SEQ ID NO:13), and $HIV-1_{LAI}$ (SEQ ID NO:14) viruses.

FIG. 11G: represents the triplex DNA sequence of the HIV-1 virus (SEQ ID NO:33). The cis-acting regions, cPPT and CTS, are boxed and printed in bold capitals.

FIG. 11 H: represents the alignment of cPPT and 3' PPT sequences in several lentiviruses. The top line corresponds to the 3' PPT sequence present in all retroviruses upstream of 3' LTR of HIV-1 (SEQ ID NO:15; HIV-2 ROD (SEQ ID NO:16); SIVmac and HIV-2 NIH-Z (SEQ ID NO:17); SIVaqm (SEQ ID NO:18); VISNA (SEQ ID NO:19); CAEV (SEQ ID NO:20); and EIAV (SEQ ID NO:21). The bottom line corresponds to the internal repetition of the PPT sequence termed the cPPT in lentivirus.

Figure 12:
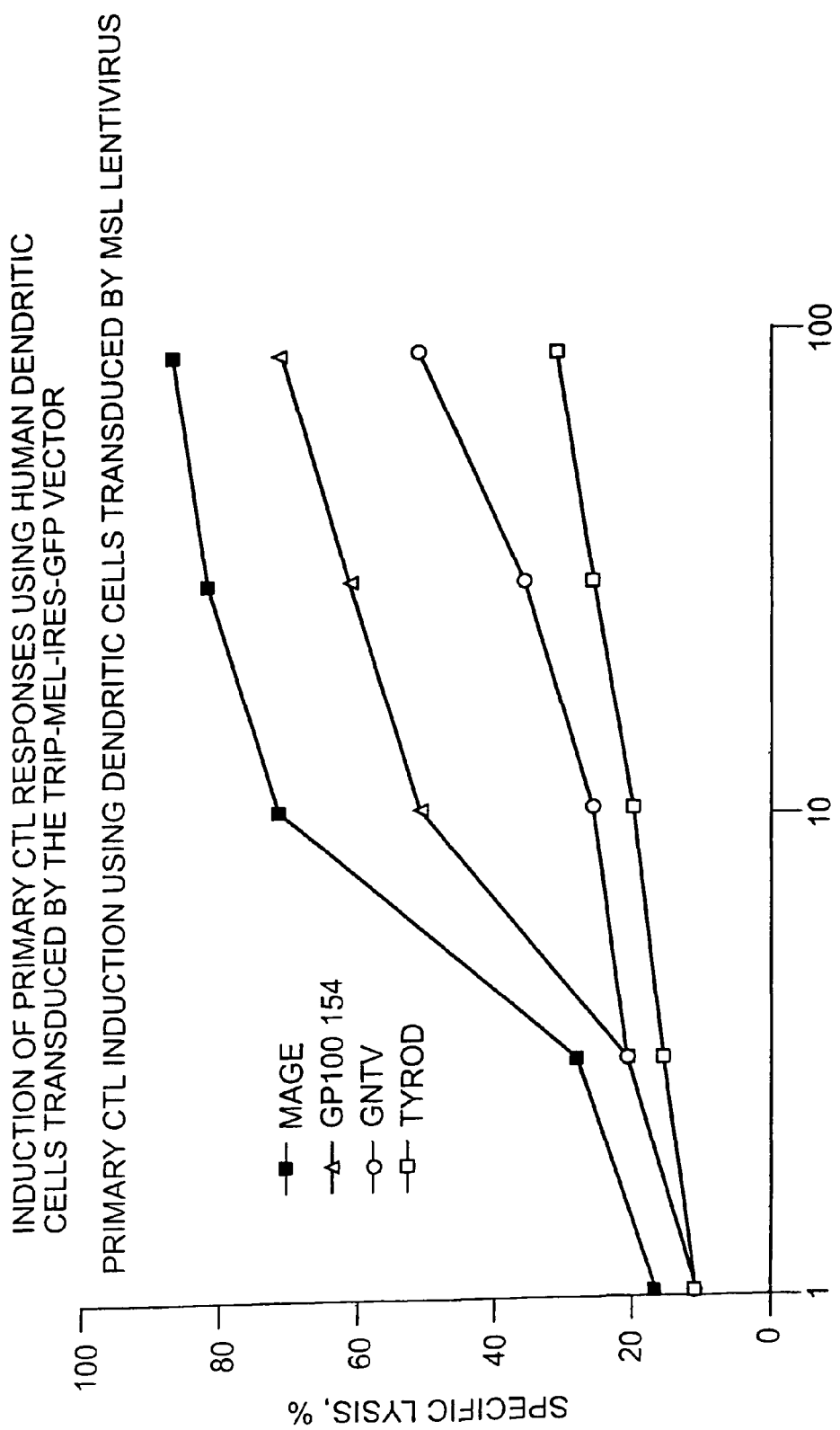

FIG. 12:

FIG. 12 represents the production of CTL in vitro from human dendritic cells transduced by the triplex vector with a melanoma CTL polyepitope constituted by epitopes the sequences of which are described in FIG. 15 as the gene of interest.

These dendritic cells were brought into contact with mononuclear cells (PBLo). The CTL activity was measured after re-stimulation by the corresponding antigenic peptides.

The effective cells/target cells ratio is shown along the abscissa.

Figure 13:
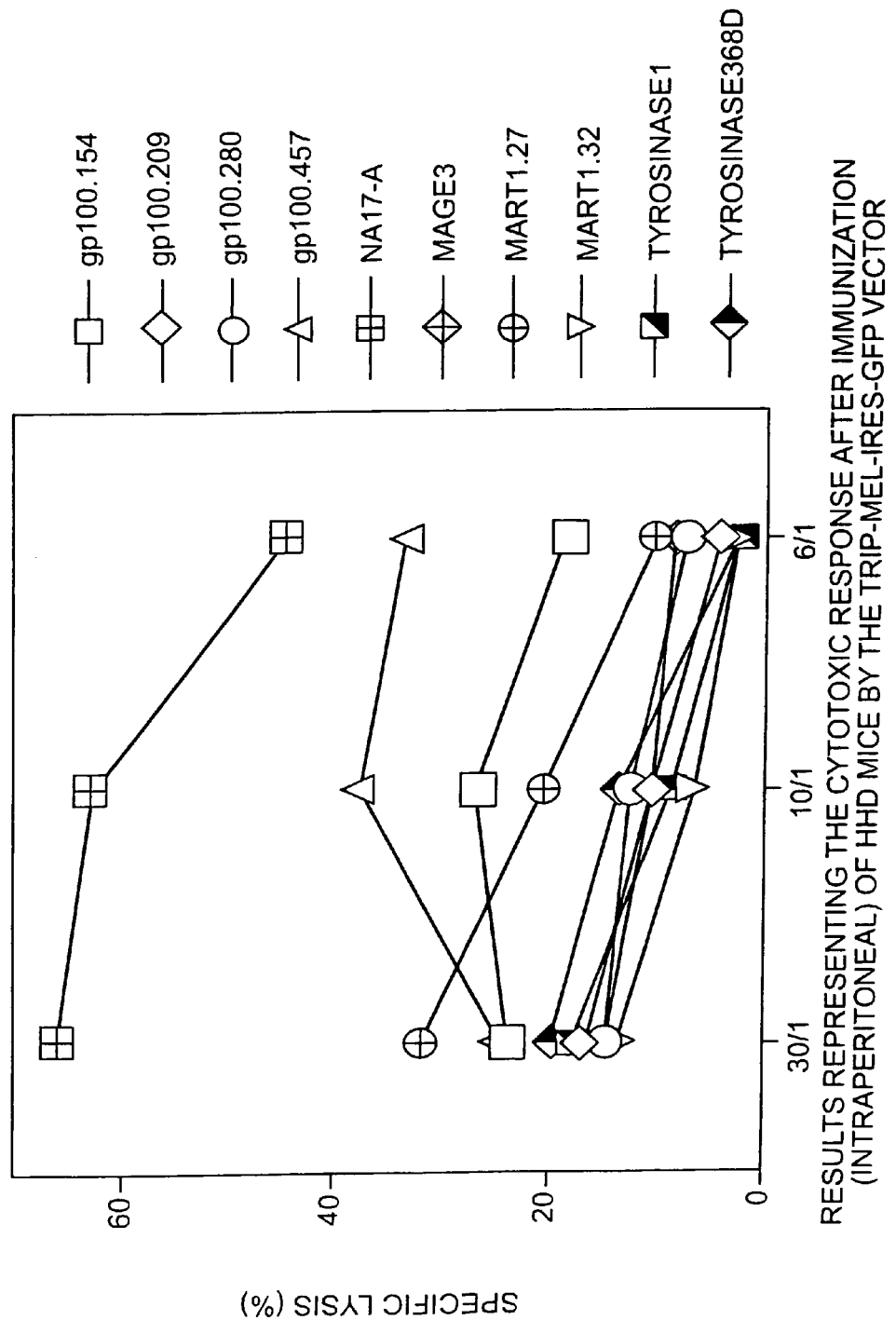

FIG. 13: Cytotoxic response after immunising mice with the TRIP.MEL-IRES-GFP vector.

Figure 14:
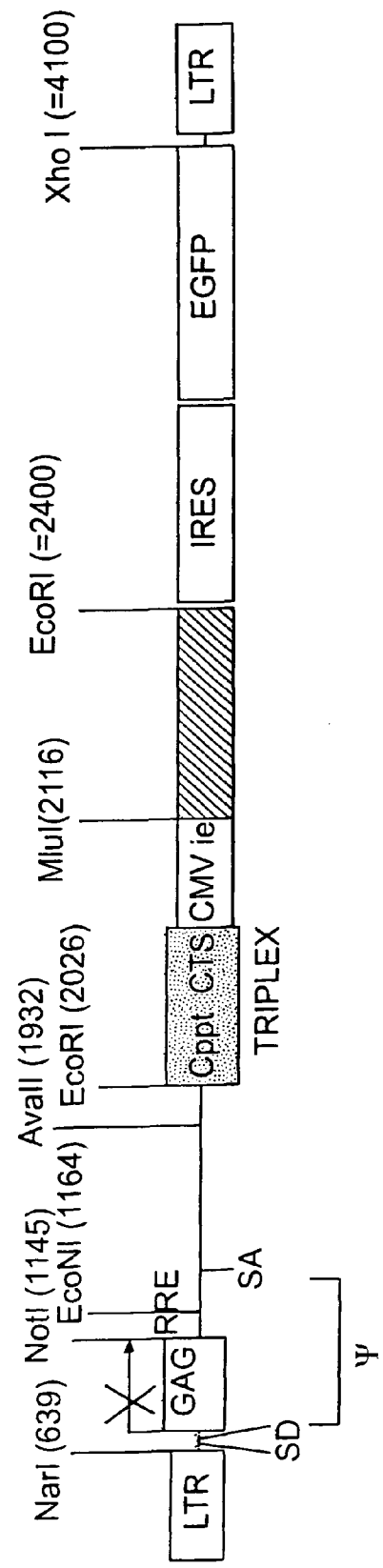

FIG. 14: Restriction map for the pTRIP.MEL-IRES-GFP vector.

The *E. coli* strain containing the pTRIP.MEL-IRES-GFP vector was deposited on 20th Apr. 1999 at CNCM, accession number 1-2185.

FIG. 15: Sequences for specific CTI HLA A2.1 melanoma epitopes included in the polyepitopic construction of the pTRIP.MEL-IRES-GFP vector. Gp100 154-162 (SEQ ID NO:22), gp100 209-217 (SEQ ID NO:23), gp100 280-288 (SEQ ID NO:24), gp100 457-466 (SEQ ID NO:25); MART-1 27-35 (SEQ ID NO:26), MART-1 32-40 (SEQ ID NO:27); Tyrosinase 1-9 (SEQ ID NO:28), Tyrosinase 368-376-D (SEQ ID NO:29); GnT-V/NA 17-A nt 36-64b (SEQ ID NO:30); MAGE-3 271-279 (SEQ ID NO:31); amino acid sequence of melanoma polyepitope (SEQ ID NO:32). The sequences of the polyepitope are underlined to distinguish each epitope.

Figure 16A:
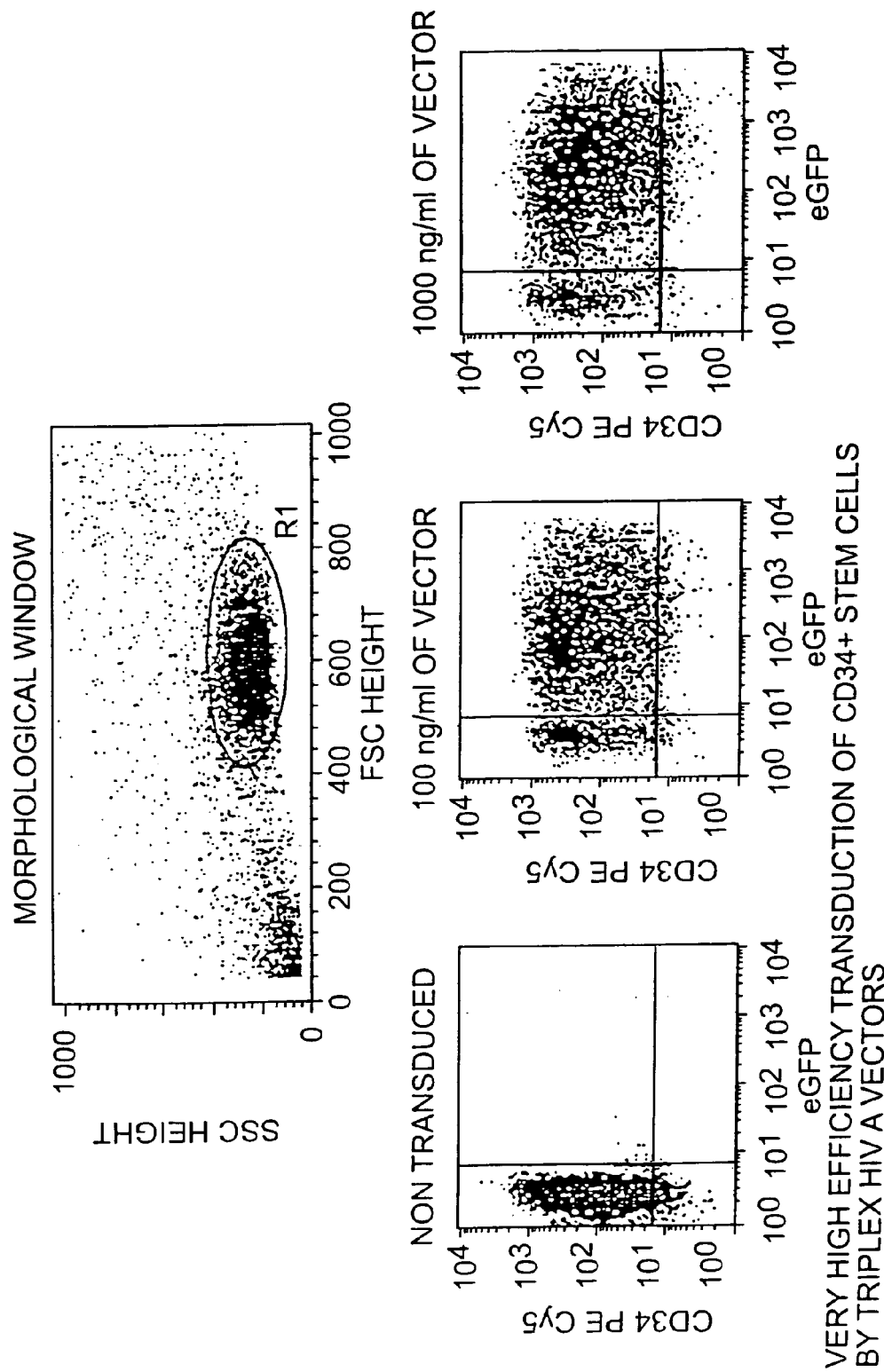
Figure 16B:
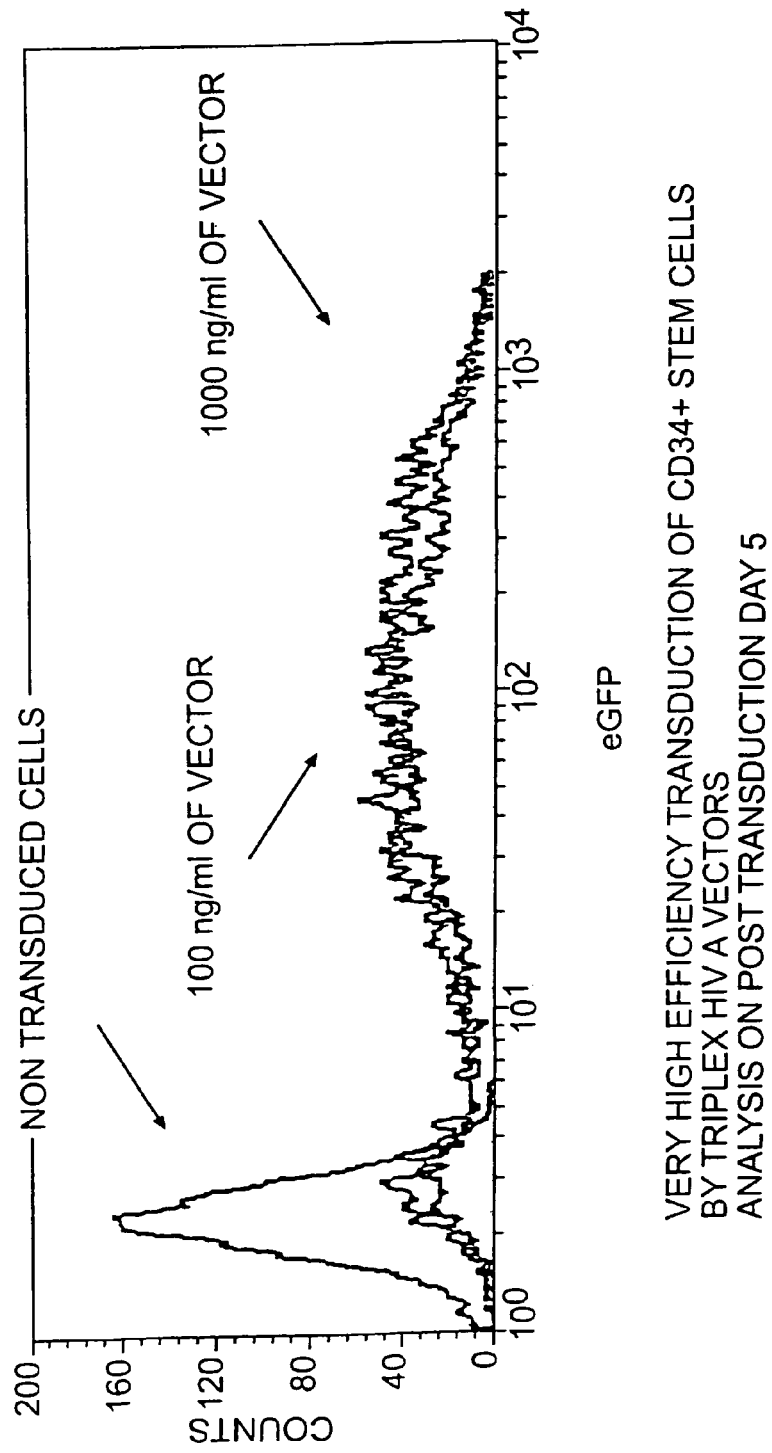

FIG. 16: Very high efficiency transduction of CD34+ stem cells by triplex HIV vectors.

Flow cytometry (FACS) analysis of transduction of the GFP gene in haematopoietic CD34+ stem cells by the TRIP-GFP vector. The percentage of CD34+ cells transduced by the TRIP-GFP vector was more than 85%. This efficiency was notably more efficient than the degree of transduction obtained previously with an HIV vector with no triplex (HR-GFP) in CD34+ cells (Miyoshi H et al, Science 1999, 283, p 682-6).

METHOD AND APPARATUS

Construction of plasmid vectors:

The pTRIP-LacZ and pTRIP-EGFP plasmids derive from the pHR'CMVlacZ construction (Naldini et al, 1996). The lacZ reporter gene of pHR'CMVlacZ was replaced by the ORF of the autofluorescent protein EGFP. The EGFP gene was amplified by PCR from the pEGFP-N1 plasmid (Clontech) using thermostable Pfu polymerase (Stratagene).

The sequences for the PCR primers used were as follows:

```
Bam EGFP:
5' cc gga tcc cca ccg gtc gcc acc 3'
(SEQ ID NO: 3)

Xho EGFP:
5' cc ctc gag cta gag tcg cgg ccg 3'
(SEQ ID NO: 4).
```

PCR amplification was carried out for 30 cycles under the following conditions:
denaturation 95° C., 30 sec;
hybridisation 50° C., 1 min;
elongation 75° C., 30 sec.

The BamHI and XhoI restriction sites were added at the 5' and 3' end respectively of the EGFP PCR fragment so as to insert it in an orientated manner into the pHR'CMV vector fragment, itself digested with BamHI and XhoI. Insertion of the EGFP PCR fragment using conventional recombinant DNA techniques (Maniatis et al, 1983) generated the pHR-EGFP plasmid.

A 184 bp fragment corresponding to the central region of the HIV-1 genome and comprising the cis-acting cPPT and CTS regions responsible for the formation of the triplex during reverse transcription of the HIV was inserted in the ClaI site of the pHR-EGFP and pHR'CMVlacZ plasmids, upstream of the CMV promoter. The central triplex region was amplified by PCR from complete proviral plasmids of the LAI HIV-1 genome comprising the wild type triplex sequence (pBRU3; Charneau et al, 1991), mutated in the cis-acting termination sequence CTS (pCTS; Charneau et al, 1994) or mutated in the cis-acting central initiation sequence cPPT (p225; Charneau et al, 1992).

The sequences for the PCR primers were as follows:

```
Nar/Eco TRIP+:
5' gtc gtc ggc gcc gaa ttc aca aat ggc agt att
cat cc 3' (SEQ ID NO: 5)

Nar TRIP-:
5' gtc gtc ggc gcc cca aag tgg atc tct gct gtc
c 3' (SEQ ID NO: 6).
```

The PCR reaction conditions were identical to those described above.

The PCR triplex fragments, digested by NarI were inserted into the ClaI site of the pHR GFP and pHR'CMV lacZ plasmids by competitive T4 DNA ligase/ClaI ligation/digestion to eliminate the self re-circularised vector during the ligation step. The orientation of the insertion was analysed by XhoI/EcoRI digestion, the EcoRI having been introduced into the 5' Nar TRIP+ PCR primer.

The resulting plasmids were termed pTRIP.EGFP in the correct orientation for the triplex and pTRIPinv.EGFP in the reverse, non functional orientation. The vectors comprising a mutated version of the triplex were termed pTRIP X.EGFP, X corresponding to the code of the starting mutant virus (AG, D, CTS or 225) (Charneau et al, J. Mol. Biol. 1994, Charneau et al, J. Virol 1992). Starting from the different plasmids pTRIP.EGFP or pTRIP X.EGFP, the EGFP gene was replaced by lacZ by orientated XhoI/BamHI exchange. The resulting plasmids were respectively termed pTRIP.Z, pTRIPinv.Z, pTRIP CTS.Z, pTRIP 225.Z.

Constructions of HR Luc and TRIP Luc Vectors

The BamHI-EGFP-XhoI fragment of the RH GFP and TRIP GFP vectors was replaced by the BamHI-Luc-XhoI fragment of the pGEM-luc plasmid (Promega) coding for luciferase.

Production of Non Infectious Vector Particles

HIV vectors were produced using a modification of the protocol described by Naldini et al, 1996. The vector particles were produced by transient co-transfection with calcium phosphate of human 293T cells (ATCC), cultivated in a DMEM (ICN), 10% FCS, penicillin, streptomycin medium. Semi confluent 175 $cm^2$ boxes were simultaneously transfected by three plasmids:

15 µg of plasmid coding for the envelope of the vesicular stomatis virus (VSV), pMD.G (Naldini et al, 1996);

30 µg of packaging plasmid, pCMVΔR8.2 (Naldini et al, 1996) or pCMVΔR8.91 (Zufferey et al, 1997);

and 30 µg of the different plasmid vectors pHR or pTRIP.

The calcium phosphate/DNA co-precipitates were left in contact with the cells for 24 hours, the medium was then collected every 24 hours up to post transfection day 3. The cellular debris of the vector supernatants was eliminated by low speed centrifugation. The vector supernatants were stored at −80° C.

Concentration of Vector Particles

The use of the very stable VSV-G envelope to pseudotype the vector particles enabled them to be concentrated by centrifugation. The supernatant vectors, collected as described above, were ultracentrifuged in 30 ml conical bottom tubes (Beckman) for 90 min at 17000 rpm at +4° C. with a SW 28 rotor (Beckman). The pellets were then taken up in 190 †µl of PBS, centrifuged for 5 min at 2000 rpm to remove non resuspendable debris, aliquoted and frozen to −80° C.

Transduction of Cells in Culture

HeLa cells (ATCC) were transduced by adding vector supernatants, which may or may not have been ultracentrifuged, in the presence of 10 µg/ml of DEAE dextran. The HeLa cells were cultivated in DMEM medium (ICN) supplemented by 10% foetal calf serum (FCS). HeLa cells were spread in an amount of 20000 cells/well onto a 96 well tray the day before infection then transduced in a final volume of 200 µl. The vector innoculum was normalised to the concentration of capsid protein (P24), calculated using a commercial ELISA test (DuPont). The gene transfer efficiency was measured using the experimental data for 24 to 48 hours post infection. The amount of transduction of vectors expressing the lacZ reporter gene was revealed either by staining with Xgal in situ (Charneau et al, 1992), or by using a luminometric reaction using a commercial kit (Boehringer) following the manufacturer's instructions. In the case of vectors expressing the reporter gene EGFP, the amount of transduction was qualitatively evaluated by direct observation of the living cells using a fluorescence microscope, on the FITC channel. The number of cells expressing the EGFP marker was quantified by flow cytometry (FITC channel). The EGFP protein was assayed by measuring the fluorescence of the cellular extract. The 96 well culture plates were rinsed twice with PBS then lysed with 100 µl of 1% NP40 PBS. The EGFP fluorescence was read using a plate fluorimeter (Victor, Wallac) with a 475 nm excitation filter and a 510 nm emission filter.

HeLa cells stopped in their cell cycle in G1/S transition were prepared under the same conditions as before with prior treatment 24 hours before with transduction with 4 µM of aphidicoline (Sigma). Under these conditions, tritiated thymidine incorporation was inhibited by more than 95%.

Ex Vivo Transduction of Primary Cells

Primary rat spinal cord cells were prepared as follows: cords from 13 to 14 day old rat embryos were dissected under a binocular magnifying glass. The tissues were kept in L15 medium (Gibco) supplemented with 3.6 mg/ml, of glucose during all the steps. The nerve cells were dissociated by incubating in trypsin (0.05% v/v) for 15 min at 37° C. Trypsic digestion was inhibited by adding 10% foetal calf serum (FCS) and centrifuging at low speed. The cellular pellet was taken up in L15 medium, 3.6 mg/ml of glucose containing 100 µg/ml of Dnasel (Boehringer) by gentle mechanical agitation. The cells were collected by low speed centrifuging through a 4% (w/v) BSA pad.

Spinal cells were seeded onto 24 well plates containing 12 mm diameter glass coverslips coated with poly-DL-ornithine (6 µg/ml) and laminin (3 µg/ml). The cell cultures were maintained in a neurobasal medium (Gibco) containing B27 supplement, 2% FCS, 0.5 mM of L-glutamine, 25 µM of beta-mercaptoethanol and 25 µM of L-glutamate. After 24 hours, the cultures were treated with 10 µg/ml of 5' fluorodeoxyuridine to prevent colonisation of the culture by non neuronal cells.

In Vivo Transduction of EGFP in the Rat Brain

Vectors expressing the marker protein EGFP were used for in vivo experiments.

The brains of 5 week old OFA spague dawley rats were injected with 2 µl of HR.EGFP vector or TRIP.EGFP vector. Firstly, the rats were put to sleep by intraperitoneal injection of Imagene 500 (Rhône Merieux). The injections were made into the striatum of each hemisphere using a stereotaxic guide, with a 5 µl Hamilton needle, at a rate of 2 µl/5 min. The rats were sacrificed one week or more after injection, by perfusion of PBS then 2% paraformaldehyde (PFA). The brains were then removed and cut to retain only the portion containing the injection point, visible by the lesion left by the needle. Post fixing with 2% PFA was carried out overnight, followed by cryoprotection with 20% then 30% sucrose. The brains were then covered with tissue-tek, frozen in solid $CO_2$ and stored at −80° C. 14 µm slices were made using a cryostat then observed with a confocal microscope.

In Vivo and In Vitro Comparison of HR Luc and TRIP Luc Vectors

One day before transduction, 20000 HeLa cells per well were spread onto 96-well plates. Transduction was carried out using the same quantity of vector particles normalised to the P24 content of the preparations: 1 ng of P24 per well, in triplicate, in the presence of 10 µg/ml of DEAE dextran. Two days after transduction, the luciferase activity was measured using a Promega kit (following the manufacturer's instructions) and a Wallac microplate measuring device (Victor).

The vectors were injected into the brain striatum of OFA spague dawley rats and C57B6 mice. 2 µl of a HR luc or TRIP luc preparation containing 25 ng of P24 was injected (n=4). The animals were sacrificed 4 days later, the striatum was removed and the luciferase activity was measured using the same technique as before, simultaneously measuring the total protein quantity (Pierce kit).

EXAMPLES

1. Fundamental Aspects. Nuclear Import of Pre-integration Complex HIV-1: Role of Central Triplex The mechanism for reverse transcription of the HIV virus differs from that of oncogene retroviruses in that the plus strand (+strand) is synthesised in two distinct halves (FIG. 1). A downstream segment is initiated at a central copy of the polypurine tract (cPPT), characteristic of lentivirus genomes. Synthesis of the upstream plus strand is terminated after a discrete displacement of the strand at the centre of the genome. Blocking the displacement of the strand by reverse transcriptase is governed by a new cis-acting sequence of the HIV genome: the CTS (central termination sequence). The final product of reverse transcription of lentiviruses is thus a linear DNA carrying a central structure spanning the strand (central triplex) over about a hundred nucleotides (Charneau et al, 1994). Specific mutagenesis of cPPT or CTS can halt initiation or central termination of synthesis of the plus strand. In both cases, mutant viruses, where the DNA is deprived of the central triplex, are defective for replication.

Analysis of a replicative defect in initiation and central termination mutants has shown that the replicative cycle of initiation mutants or central reverse transcription termination mutants aborts during a posterior step in synthesis of viral DNA and posterior to routing the reverse transcription complex towards the nuclear envelope. When the structure of the viral DNA present in the infected cells is analysed, it is seen that the phenotypes of the initiation and termination mutants are similar. In both cases, the global reverse transcribed DNA content is not affected by mutations in cPPT or CTS. In contrast, an accumulation of linear non integrated DNA is observed, along with very little integrated provirus or circles with 1 or 2 LTRs formed over the same period. Nucleus/cytoplasm fractionation experiments and nucleus permeabilisation experiments have then shown that these linear DNA molecules are associated with the nucleus, but that their integration and/or circularisation can only occur after dissolving the nuclear envelope, which clearly indicates that the viral DNA of the mutants is kept outside this envelope. Further, nuclease attack experiments on the purified nuclei of cells infected with DnaseI immobilised on gold beads again show an accumulation of mutant linear DNA on the cytoplasmic surface of the nuclear membrane. Finally, precise quantification of the integrative capacity of the linear DNA molecules provided or not provided with a wild type central triplex have recently shown that the central triplex does not influence integration of linear DNA into a heterologous DNA target in vitro.

The replicative defect of viruses mutated for initiation or central termination of reverse transcription thus concerns the nuclear import of their pre-integration complex and more precisely the step for translocation through nuclear pores. Lentiviruses, in particular the HIV virus, have developed an original strategy for reverse transcription wherein the aim is to create the triplex at the centre of non integrated DNA molecules, an indispensable determinant for entry of the viral genome into the nucleus of an interphase cell. This mechanism distinguishes lentiviruses from all other retroviruses wherein access of DNA to the integration site depends on the disorganisation of the nuclear membrane during mitosis.

2. Generation of Lentiviral Vectors Containing Cis-acting Sequences Responsible for Triplex Formation

2-1 Principle and Importance of Lentiviral Vectors

The generation of effective lentiviral vectors assumes knowledge of the determinants responsible for active nuclear import and thus infection of non mitotic cells.

The discovery of the involvement of the triplex in the nuclear import of the HIV-1 genome has important consequences for the construction of effective lentiviral vectors. It assumes conservation in the vector construction of cis-acting sequences responsible for the formation of triplex DNA during lentiviral reverse transcription. The vectorological application of this fundamental research consists of adding the central cPPT-CTS region to lentiviral constructions so as to create the triplex DNA structure during reverse transcription of the vector genome. It should be noted that many attempts at constructing a lentiviral vector have been made, based on the same principle as vectors derived from oncovirus (in general MoMLV), and have proved to be disappointing at least as regards the infectious titre. These vectors are replacement vectors, i.e., the ensemble of the viral genome is deleted then replaced, between the two LTRs and the packaging sequence, by the reporter gene or the gene of therapeutic interest (Miller et al, 1989). According to the inventors, this type of construction is not optimal in the case of lentiviral vectors because of the need for the central cPPT-CTS region for nuclear import of the viral DNA. However, HIV vectors constructed on the same principle as retroviral vectors derived from oncovirus, but pseudotyped by the highly fusiogenic envelope of the vesicular stomatitis virus (VSV-G) and concentrated by ultracentrifuging, enable in vivo transduction of rat neurons (Naldini et al, 1997; Blomer et al, 1997) and of the liver and differentiated muscle (Kafri et al, 1997). However, complementation experiments with human pulmonary epithelium xenografts with these HIV vectors coding for the CFTR (cystic fibrosis) gene have proved to be very disappointing. The essential portion of the DNA vector in this tissue remains in the form of linear non integrated DNA, thus revealing a probable defect in nuclear import (Goldman et al, 1997; see the section "Influence of central triplex on the amount of nuclear import of vector DNA").

2.2 Construction and Production of "Triplex" HIV Vectors

In order to test the importance of the triplex structure in a vector system, the inventors took as a basis the constructions described by Naldini et al. In this system (FIG. 2), HIV vector particles are produced by transient co-transfection of three plasmids: a packaging plasmid expressing the whole of the viral proteins with the exception of the HIV envelope, a plasmid expressing the VSV-G envelope and a plasmid vector, pHR-CMVlacZ, comprising the LTRs of HIV, the bipartite packaging signal of HIV and a lacZ expression cassette. Firstly, the lacZ reporter gene was replaced by a gene coding for a highly fluorescent version of EGFP (E green fluorescent protein), more practical for in vivo transduction studies. The central region of the HIV-1 LAI genome comprising the cis-acting cPPT and CTS sequences, responsible for triplex formation, was amplified by PCR then inserted into the ClaI site, in the vector construction pTRIP-EGFP. Insertion of the wild type triplex in the correct orientation generated the pTRIP-EFGP vector; in the reverse orientation (non functional), it generated the pTRIPinv-EGFP vector.

2-3 Rapid and Sensitive Test for Detecting a Helper Virus in Lentiviral Vector Preparations: Absence of Infectious Helper Viruses in "Vector Supernatants"

The production of vector particles from three independent plasmids with a minimum of homologous sequences could minimise the probability of generating a helper virus which was capable of replication. Further, the packaging construction had been deleted for the HIV envelope and for the ensemble of the genes said to be accessory to replication (Vif, Vpr, Vpu, Nef). The packaged vector genome no longer contained HIV other than the 2 LTRs, the sequences necessary for packaging of the triplex sequence. However, each vector stock was tested for the presence of infectious helper viruses. MT4 cells were infected in triplicate, on a microplate, overnight, then washed extensively and taken up into culture again for 5 days in order to amplify the innoculum. P4 indicator cells (HeLa CD4 LTR-lacZ) were then infected with MT4 cells and their supernatant for 3 days to detect the infectious particles produced. Finally, in situ Xgal staining was carried out. In this manner, any infectious particle produced was detectable in the form of a blue scintillation. This sensitive protocol could detect an HIV innoculum of 0.25 pg of P24, i.e., about 3200 physical particles. Knowing that in the case of HIV, a single particle in 1000 or even in 10000 is infectious, the protocol can probably detect a single infectious particle.

The vector supernatants were systematically deprived of infectious HIV particles.

2-4 Effect of Triplex on Transduction Efficiency by Vectors In Vitro

Firstly, (FIG. 3), the effect of inserting the central triplex on HeLa cell transduction was measured. HeLa cells were infected with a transfection supernatant from a wild type central triplex vector (TRIP GFP), a vector without this sequence (HR GFP) or with a mutant triplex sequence (TRIP GFP D). The D mutant was a cPPT mutant which prevented central initiation of the +strand and thus the formation of the central triplex (FIG. 3). Infections were carried out with supernatants containing the same quantity of particles normalised to the quantity of capsid protein P24.

GFP transduction in HeLa cells was increased in the presence of a wild type triplex and dropped to the base level in the presence of a non functional triplex.

This increase in titre could be quantified using the lacZ reporter gene (FIG. 4). These cells were transduced in triplicate by normalising with respect to the quantity of P24 protein. Transductions were carried out using cells blocked or not blocked in division with aphidicoline, which blocks G1/S cells. The vectors used were HRZ (no triplex), TRIP Z (with triplex), TRIP Z inv (the triplex sequence was in the reverse direction, non functional, and did not lead to formation of a central triplex).

FIG. 4A: The gains in transduction of βgal by vectors containing the triplex was 6 to 10 times. It was lost when the triplex was not formed (TRIP Z inv).

FIG. 4B: The effect of triplex on transduction of βgal was independent of cell division: similar results were obtained with cells in division or blocked with aphidicoline.

Further, the same results were obtained with HeLa cells, when the packaging plasmid used during production of the vector particles was or was not deleted in the accessory genes Vif, Vpr, Vpu, Nef.

2-5 Effect of Triplex on Efficiency of Transduction by Ex Vivo Vectors

The impact of the triplex on EGFP transduction in primary non mitotic cells was then measured. Primary explants from rat spinal cord enriched in neurons were transduced with ultracentrifuged vector supernatants. The transductions were carried out with less than 10 µl of ultracentrifuged vector, containing the same number of particles, normalised to the number of ng of P24 capsid protein.

FIG. 6: The vector with a triplex sequence transduced a much larger number of rat primary spinal cord explant cells than the vector without triplex.

2-6 Impact of Triplex on In Vivo Transduction in the Brain

The effect of triplex on in vivo EGFP transduction was then measured by direct injection into the rat brain. The same volume (2 µl) of vector supernatant with or without triplex containing the same quantity of P24 protein was injected into the striatum. While a large number of transduced cells was detected in rats injected with the vector with triplex (FIG. 7a), it was only possible to detect a few cells expressing EGFP in the brains of rats injected with the vector without triplex, at the exact point of the injection, visible by the lesion left by the needle.

In FIG. 7b, the construction of the HIV vectors (with or without triplex DNA sequence) which express the reporter gene luciferase (HR Luc and TRIF.Luc) enabled the impact on gene transduction in the brain to be precisely quantified. In vitro, an increase by a factor of 8 was observed in HeLa cells (FIG. 7-b1). An analogous benefit was obtained after direct injection in vivo into the brain striatum of the rat (FIG. 7-b2) or mouse (FIG. 7-b3).

2-7 Impact of Triplex on Nuclear Import of Vector Genome

A test which enabled the ensemble of the forms of DNA vector in the transduced cell to be followed over time was developed by the inventors: linear DNA, circles with 1 or 2 LTRs but also integrated provirus. This test is based on detecting viral DNA by Southern blot using a cleaving strategy and a choice of probe enabling the different forms of retroviral DNA to be differentiated (see FIG. 8). The total DNA of the infected cells or cells transduced by the vectors was digested by one or more restriction enzymes to detach an internal fragment, common to all forms of retroviral DNA or vector DNA present in the cells (linear non integrated DNA, circularised DNA with one or two LTRs and integrated provirus). In the case of a vector, the enzymes selected were Eco NI and Ava II. When using as a probe a fragment generated by PCR exactly spanning the Eco NI site, several bands corresponding to the different forms of DNA appear. The internal fragment enabled the total vector DNA present in the cells to be calculated after quantification using a Phosphorimager. A 1.16 kb fragment corresponded to the distal fragment of non integrated linear DNA, a further 3.3 kb corresponded to non integrated circles. After quantifying the signals with the Phosphorimager, the degree of nuclear import was indicated by the percentage of viral DNA integrated and in the circular form (nuclear viral DNA) with respect to the linear cytoplasmic DNA. The first preliminary blots showed an intracellular DNA profile characteristic of a lack of nuclear import in the case of vectors deprived of triplex or wherein the central region of the HIV-1 genome had been inserted in reverse. The intensity of the signal corresponding to linear DNA was equivalent to that of the total signal DNA 48 hours post infection. In other words, processing of the DNA vector was mainly blocked in the non integrated linear stage, and very few molecules were integrated (FIG. 9). In contrast, in the case of vectors with a triplex, only a little linear DNA subsisted after 48 hours, indicating that the major portion had been imported into the nucleus of the transduced cell, then integrated.

2-8 Study of the Effect of the Position of the DNA Triplex on Vector Construction All lentiviruses contain cis-acting cPPT and CTS sequences responsible for triplex formation during reverse transcription. In all cases, this triplex was found within a few nucleotides of the centre of the linear DNA genome. This central position of the triplex could be important for the optimum function of this determinant of translocation through the nuclear pore. With the vector constructions produced, the triplex sequence had been inserted just upstream of the transcriptional unit of the reporter gene. Depending on the size of the reporter gene, this triplex was found at a greater or lesser distance from the centre of the linear vector DNA genome. In the case of the reporter gene EFGP (0.7 kb), the triplex is very close to the centre of the construction; while in the case of lacZ (3.1 kb), it is further away (FIG. 2). In both cases, the presence of the triplex induced a large gain in titre in the supernatant vectors. Thus there exists a certain "flexibility" in the position of the triplex on the vector genome. However, vectors coding for EGFP have been clearly shown to be more effective than those coding for lacZ. It is thus possible that an ideally positioned triplex can result in an additional gain in titre. In order to test this hypothesis, the inventors undertook to clone, in the place of reporter genes, a bank of fragments of random size (partial Sau3A digestion), the size distribution of the cloned fragment being analysed before and after transduction of the target cells. If the central position of the triplex is important to its function, constructing a symmetrical vector with respect to the triplex would be important. It is possible to overcome this obstacle by inserting the transcriptional unit of the vector into the U3 region. After reverse transcription, the transgene will be duplicated either side of the triplex before being integrated, thus providing the triplex with a precisely central position.

2-9 In Vivo Transfer in Different Differentiated Tissues

The capacity of "triplex" lentiviral vectors to efficiently and stably transduce the affected differentiated tissues in various genetic disorders was studied. The potential of these vectors in the brain, and in different tissues such as muscle, pulmonary epithelium and liver in the rat or mouse was studied. Qualitative responses could be obtained relatively rapidly using the EGFP reporter gene. Quantitative measurements of the impact of the triplex on the degree of transduction of these tissues were possible using the reporter gene luciferase. Further, the capacity of these vectors to transduce totipotent stem cells of human haematopoietic tissue could be evaluated, either from purified CD34+ cells or from total cord blood cells.

2-10 High Efficiency Gene Transfer in Haematopoietic Stem Cells by Triplex HIV Vectors Haematopoietic stem cells are very important targets for the treatment of a large number of genetic disorders connected with the blood, with muscular disorders or with neurological disorders, and with infectious diseases. The major difficulty for gene transfer by retroviral vectors derived from oncovirus such as MoMLV into these cells is that they only rarely divide and that inducing mitosis by a cytokine treatment is generally accompanied by a loss of totipotency. FIG. 16 shows the results of transduction of the GFP gene in CD34 stem cells by the TRIP-GFP vector showing expression of GFP in more than 85% of the cells. The efficiency of transduction of CD34 stem cells by the vector without triplex, HR-GFP, was very low (Miyishi H et al, Science 1999, 283, p 682-6). Since the CD34 stem cells were transduced immediately after their purification, their clonogenic capacity remained intact.

2.11 Use of Lentiviral Vectors with a Triplex Sequence for Transduction of Embryonic Cells: Application to the Construction of Transgenic Animals or Modified Cell Lines Retroviral vectors are potentially important tools for the construction of transgenic animals via egg transduction (Rubenstein et al, 1986, PNAS, 83, p 366-368) or ES cells (Friedrich and Soriano, 1991, Genes Dev. 5, p 1513-1523). Using lentiviral vectors can increase the efficiency of transduction of these totipotent cells. Our preliminary results for transduction of mouse embryo cells via the TRIP-GFP vector show a high efficiency of transfer of the GFP gene but also complete extinction of transcription of the GFP transgene. Certain viral sequences, in particular the primary binding site (PBS), are suspected of intervening in this extinction of expression. In order to overcome this obstacle, self-deleting vectors for these viral sequences, focused on the CRE/Lox specific recombination system (Choulika et al, 1996, J. Virol. 70, p 1792-98) were constructed.

2.12 Immunogenic Composition with Prophylactic and/or Therapeutic Applications

A Novel Immunisation Strategy: Triplex Lentiviral Vectors

Introduction

The role of T lymphocytes in the antitumoral and antiviral response has been documented in many murine experimental systems and also in man. Different vaccine strategies aim at inducing a protective cytotoxic response against tumours or infectious agents. Lentiviruses have the capacity of crossing nuclear pores and as a result are much better cell transduction vectors. In vitro and/or in vivo cell transduction can lead to the presentation by such cells of epitopes of tumoral and/or viral antigens which as a result induce a specific cellular immunity. For these reasons, the inventors have studied the immunogenic capacity of recombinant triplex lentiviral vectors using either in vitro transduced dendritic cells or direct in vivo administration to "humanised" mice by expression of HLA-A2.1 (Pascolo S et al, 1997). This "HLA-A2.1 pure" HHD mouse is the best animal model for studying the restricted HLA-A2.1 cytotoxic response and has been proposed for carrying out preclinical immunotherapy studies. The whole of our results clearly shows the immunogenic capacity of triplex lentiviral vectors containing tumoral epitopes and thus triplex lentiviral vectors represent a novel immunotherapeutic strategy.

Initial Study: Comparison of Different Vaccine Strategies

Different vaccine strategies were initially compared using HHD mice. By arbitrarily selecting 5 tumoral epitopes, the inventors compared five immunisation strategies applicable for human clinical practice: (i) synthetic peptides in incomplete Freund's adjuvant; (ii) lipopeptide (iii) recombinant yeast Ty particles in which, independently, the epitopes were fused at the C terminal end to the P1 protein; (iv) intramuscular administration of naked DNA coding the glycoprotein of the hepatitis B virus fused to epitopes in its pre-S2 portion; (v) intravenous injection of dendritic cells charged with peptides after expansion and differentiation in vitro from marrow cells. Having observed that the injections of particular structures (recombinant yeast Ty) or naked recombinant DNA coding an S glycoprotein of the hepatitis B virus (refer to International patent application WO-A-95/11307, published May 25, 1995) were the most effective strategies for inducing cytolytic responses, by inserting a polyepitopic moiety derived from melanoma (10 distinct o epitopes) into this glycoprotein, the inventors have documented the possibility of simultaneously inducing cytolytic responses against 5 epitopic peptides out of 10 in all of the test mice.

The particular Ty or naked DNA antigens proved to be effective strategies for inducing cytotoxic responses. However, the large scale production of Ty particles is difficult. Further, it is feared that introducing multiple hydrophobic epitopes into the pre-S2 segment of the hepatitis B virus glycoprotein will entrain a large reduction in the production of particles by CHO cells (the current method for preparing a hepatitis vaccine). The recombinant lentiviruses (HIV-1) produced in the form of largely deleted pseudotypes but conserving the triplex DNA sequence have the capacity to traverse the nuclear membrane of non dividing cells and represent a novel vaccine strategy which is potentially more effective with respect to the vaccine strategies cited above.

Method, Apparatus and Results

Transgenic Mice

HHD mice express a monocatenary construction in which the peptide presentation (a1, a2) domains of the HLA-A2.1 molecule are covalently associated at the N-end to the human (β-2 microglobulin. The a3 domain and the intracytoplasmic portion of the HLA-A2.1 molecule were replaced by their equivalent in the H-2D$^b$ molecule (Pascolo S et al, 1997). These mice enabled the immunogenicity of epitopic peptides and the different vaccine strategies to be studied and compared.

Construction of TRIP-MEL IRES GFP Vector

Firstly, a bicistronic TRIP-IRES-GFP vector was constructed. The EcoRI site of the TRIP-IRES-GFP vector was filled with T4 DNA polymerase creating the TRIP -deltaE-GFP vector. Then a fragment of about 1.2 kb, BamHI-BstXI-SnaBI-EcoRI-IRES -EGFP-Xhol, was cloned in the place of the BamHI-EGFP-Xhol fragment. The fragment containing the IRES-EGFP (internal ribosome entry site) was generously donated by Dr Yongwhon Choi (Rockefeller University, NY, USA). A fragment containing a Kozac consensus sequence and a melanoma CTL polyepitope was generated by PCR, using the pBS mel poly matrix with pfu polymerase and the following oligonucleotides: 5Bglmlu Mel: 5' cc aga tct acg cgt gcc acc atg gct gct ggt 3' (SEQ ID NO:7); 3RIMeI: 5' CG GAA TTC GAC CTA AAC GCA ACG GAT G 3' (SEQ ID NO:8). The mel PCR fragment was then digested with BglII and EcoRI and cloned to the BamHI and EcoRI sites of the TRIP-deltaE-IRES-GFP vector creating the TRIP-MEL-IRES-GFP vector.

In Vitro Transduction Efficiency of Dendritic Cells (DC) by GFP Lentiviral Vectors with or without Triplex Murine DCs were obtained from the marrow of transgenic HHD mice in the presence of IL4 and GM-CSF. Human DCs were obtained from healthy HLA-A2.1 haplotype donors (see below). These cells were transduced by LV vectors with or without triplex using different concentrations (75, 150 and 300 ng P24 of lentiviral vector per 5×10$^5$ cells).

The expression of GFP in the DCs was measured by FACS on days 2, 5 and 10. The values in terms of the average fluorescence intensity corresponding to the cell transduction efficiency have shown that triplex lentiviral vectors have 5 to 7 times the transduction capacity for human DCs compared with lentiviral vectors without triplex.

Induction of Primary CTL Responses Using Human Dendritic Cells Transduced by the TRIP-MEL-IRES-GFP Vector Immature human DCs were obtained from healthy HLA-A.2.1 haplotype donors in the presence of GM-CSF and IL13 (IDM, Paris, France). Immunophenotyping of these cells by monoclonal antibodies against CD1, CD4, HLA-ABC, HLA-DR, CD80, and CD86 showed their immature nature with a DC purity of more than 91%.

The DCs obtained were transduced by the TRIP-MEL-IRES-GFP vector in a concentration of 100 ng P24/vector per 1×10$^6$ cells. The efficiency of DC transduction by TRIP-MEL-IRES-GFP was studied by, measuring the expression of GFP by FACS. Mononuclear cells (MNC) from the same donor were stimulated by the previously transduced DCs. After three stimulations, the cytotoxic activity of these cells was tested on T2 cells individually charged with 4 epitopic peptides using a conventional 4 hour CTL test. The epitopic peptides Mage-3, gp100.154, GnTV/NA17/A, and tyrosinase 368-D were selected because of their high immunogenicity in the previous experiments.

Specific cytotoxic responses were observed against all of the epitopes tested. The lysis percentage for each epitope is shown in FIG. 12.

Direct Immunisation of HHD Mice by the TRIP-MEL-IRES-GFP Vector

HHD mice were immunised by 2.5µ/P24 of the TRIP-MEL-IRES-GFP vector per mouse subcutaneously (SC), intravenously (IV) and intraperitoneally (IP). On immunisation day 11, spleen cells from each mouse were individually stimulated by epitopic melanoma peptides for 6 days wherein 2 days were in the presence of 10% TCGF. The lytic activity of these cells was then tested on RMAS cells charged with the corresponding peptides or on HeLa-HHD cells transduced by the TRIP-MEL-IRES-GFP vector.

The results obtained for each mouse are represented in terms of the specific lysis of RMAS cells (Table 1) and of transduced HeLa-HHD cells (Table 2). The best results were obtained after administering the vector by SC and IP routes both in terms of lysis and the number of responses simultaneously induced in a given mouse. The remarkable fact is that the majority of mice immunised by the IP route developed cytolytic responses against all the epitopic peptides (FIG. 13).

TABLE 1

Specific cytotoxic response after immunisation with TRIP-MEL-IRES-GFP vector
Specific lyses obtained after immunisation of HHD mice by LV containing a
melanoma polyepitope. In vitro individual SC stimulation for each mouse
on day 8 in the presence of TCGF and peptide

|    | Mouse | gp154 | gp209 | gp280 | gp457 | G-nTV | Mage-3 | Mart 1.27 | Mart1.32 | Tyro-1 | Tyro368-D |
|----|-------|-------|-------|-------|-------|-------|--------|-----------|----------|--------|-----------|
| SC | 1     | 25    | 4     | 13    | 8     | 54    | 17     | 17        | 4        | 4      | 10        |
|    | 2     | 44    | 1     | 5     | 11    | 89    | 10     | 11        | 4        | 3      | 6         |
|    | 3     | 39    | 0     | 19    | 21    | 81    | 29     | 26        | 6        | 4      | 0         |
| IV | 1     | 7     | 7     | 1     | 8     | 25    | 5      | 8         | 3        | 4      | 3         |
|    | 2     | 10    | 8     | 0     | 13    | 70    | 13     | 16        | 5        | 9      | 14        |
|    | 3     | 24    | 6     | 5     | 5     | 65    | 15     | 16        | 3        | 11     | 10        |
|    | 4     | 5     | 3     | 13    | 12    | 14    | 10     | 5         | 0        | 3      | 0         |
| IP | 1     | 30    | 10    | 2     | 3     | 57    | 9      | 6         | 4        | 3      | 2         |
|    | 2     | 63    | 8     | 7     | 17    | 72    | 11     | 19        | 9        | 7      | 7         |
|    | 3     | 21    | 7     | 8     | 16    | 72    | 14     | 32        | 0        | 7      | 7         |

Target cells: RMAS charged with corresponding peptides Effector/target ratio: 30

TABLE 2

Specific cytotoxic response after immunisation with TRIP-MEL-IRES-GFP vector
Cytolytic responses of HHD mice immunised by SC, IV or OP routes with the
TRIP-MEL-IRES-GFP vector. Results obtained for HeLa-HHD cells expressing
the melanoma polyepitope.

|    | gp154 | gp209 | gp280 | gp457 | G-nTV | Mage-3 | Mart 1.27 | Mart1.32 | Tyro-1 | Tyro368-D |
|----|-------|-------|-------|-------|-------|--------|-----------|----------|--------|-----------|
| SC | 2     | 18    | 15    | 24    | 62    | 15     | 20        | 12       | 20     | 18        |
| IV | 8     | 10    | 15    | 23    | 50    | 14     | 29        | 10       | 10     | 18        |
| IP | 24    | 18    | 15    | 25    | 62    | 15     | 32        | 14       | 18     | 20        |

Target cells: HeLa-HHD transduced by the TRIP-MEL-IRES-GFP vector Effector/target ratio: 30

CONCLUSION

The results demonstrate the capacity of triplex lentiviral vectors to induce highly effective immune responses. Their immunogenic power has been demonstrated not only in vitro on human dendritic cells but has also been evaluated in the transgenic HLA-A2.1 mouse using different modes of administration. Remarkably, specific CTL responses have been obtained for the ten CTL epitopes contained in the melanoma polyepitope. The lysis percentages against melanoma antigens were also higher than those obtained with the same HHD mice with other vaccine strategies such as lipopeptides, recombinant vaccine or DNA vaccination with HBV pseudoparticles. As a result, vaccine strategies based on triplex lentiviral vectors are applicable to a variety of tumoral or infectious disorders.

4—REFERENCES

Blomer U Naldini L. Kafri T, Trono D, Verma I M, Gage F H Highly efficient and sustained gene transfer in adult neurons with a lentivirus vector. J Virol. 1997 September; 71(9): 6641-6649.

Charneau P, F. Clavel. 1991. A single-stranded gap in human immunodeficiency virus unintegrated linear DNA defined by a central copy of the polypurine tract. J. Virol., vol.65, N° 5, 2415-2421.

Charneau P., Alizon M. and Clavel F. (1992). A second origin of plus strand synthesis is required for optimal HIV replication. J. Virol. 66: 2814-2820.

Charneau P. G. Mirambeau, P. Roux, S. Paulous, H. Buc, F. Clavel. 1994. HIV-1 reverse transcription: a termination step at the center of the genome. J. Mol. Biol., vol. 241,651-662.

Goldman M J, Lee P S, Yang J S, Wilson J M. Lentiviral vectors for gene therapy of cystic fibrosis. Hum Gene Ther. 1997 Dec. 10; 8(18): 2261-2268.

Heyman T., Agoutin B., Friant S., Wilhelm F. X., Wilhelm M. L., 1995, Plus-Strand DNA Synthesis of the Yeast Retrotransposon Ty1 is Initiated at Two Sites, PPT1 Next to the 3' LTR and PPT2 Within the pol Gene. PPT1 is sufficient for Ty1 Transposition. J. Mol. Biol., vol. 253, 291-303.

Kafri T, Blomer U, Peterson D A, Gage F H, Verma I M. Sustained expression of genes delivered directly into liver and muscle by lentiviral vectors. Nat Genet. 1997 Nov; 17(3): 314-317.

Naldini L, Blomer U, Gage F H, Trono D, Verma I M. Efficient transfer, integration, and sustained long-term expression of the transgene in adult rat brains injected with a lentiviral vector. Proc Natl Acad Sc USA. 1996 Oct. 15; 93(21): 11382-11388.

Naldini L, Blomer U, Gallay P, Ory D, Mulligan R, Gage F H, Verma I M, Trono D. In vivo gene delivery and stable transduction of nondividing cells by a lentiviral vector. Science. 1996 Apr. 12; 272(5259): 263-267.

Miller A D, Rosman G J. Improved retroviral vectors for gene transfer and expression *BioTechniques* (1989), Vol 7, p 980-990.

Pascolo S., N. Bervas, J. M. Ure, A. G. Smith, F. A. Lemonnier and B. Pérarnau. 1997. HLA-A2.1-restricted education and cytolytic activity of CD8+ T lymphocytes from β2 microglobulin (β2m) HLA-A2.1 monochain transgenic, H-2D$^b$, β2m double knockout mice. J. Exp. Med. 185, 2043-2051.

Poeschla E. M., Wong Staal F., Looney D. J. Efficient transduction of nondividing human cells by feline immunodeficiency virus lentiviral vector—Nature Medicine, vol. 4, n° 3: 354-357.

Zufferey R, Nagy D, Mandel R J, Naldini L, Trono D. Multiply attenuated lentiviral vector achieves efficient gene delivery in vivo. Nat Biotechnol. 1997 Sep; 15(9): 871-875.

The invention claimed is:

1. A non-replicative, recombinant retroviral vector, which does not encode functional Gag, Pol, and Env proteins, for the transduction of a transgene into a cell comprising:
a transgene under the control of sequences regulating transcription;
regulatory signals for reverse transcription and packaging; and
a lentiviral cis-acting central initiation region and a lentiviral cis-acting termination region, such that a triplex DNA is formed during reverse transcription,
wherein the triplex DNA stimulates the nuclear import of the transgene into the nucleus of a cell transduced with said vector.

2. The vector of claim 1, wherein the cis-acting central initiation region and a cis-acting termination region are derived from a human immunodeficiency virus type 1 genome.

3. The vector of claim 1, wherein the sequences regulating transcription of the transgene are non-retroviral sequences.

4. The vector of claim 3, wherein the sequences regulating transcription of the transgene comprise a cytomegalovirus promoter.

5. The vector of claim 3, wherein the sequences regulating transcription of the transgene comprise a phosphoglycerate kinase promoter.

6. The vector of claim 3, wherein the sequences regulating transcription of the transgene comprise an elongation factor 1α (EF1α) promoter.

7. The vector of claim 1, wherein the regulatory signals for reverse transcription and packaging are derived from a human immunodeficiency virus type 1 genome.

8. The vector of claim 2, wherein the regulatory signals for reverse transcription and packaging are derived from a human immunodeficiency virus type 1 genome.

9. The vector of claim 3, wherein the regulatory signals for reverse transcription and packaging are derived from a human immunodeficiency virus type 1 genome.

10. The vector of claim 1, wherein the vector is a plasmid.

11. The vector of claim 1, wherein the vector is a phage.

12. The vector of claim 1, wherein the vector is a YAC.

13. The vector of claim 1, wherein the vector is contained in a recombinant vector particle.

14. The vector of claim 13, wherein the recombinant vector particle comprises human immunodeficiency virus type 1 Gag, Pol, and Env polypeptides.

15. The vector of claim 13, wherein the recombinant vector particle comprises human immunodeficiency virus type 1 Gag and Pol polypeptides, and vesicular somatitis virus Env polypeptides.

16. The vector of claim 2, wherein the vector is contained in a recombinant vector particle.

17. The vector of claim 16, wherein the recombinant vector particle comprises human immunodeficiency virus type 1 Gag, Pol, and Env polypeptides.

18. The vector of claim 16, wherein the recombinant vector particle comprises human immunodeficiency virus type 1 Gag and Pol polypeptides, and vesicular somatitis virus Env polypeptides.

19. The vector of claim 7, wherein the vector is contained in a recombinant vector particle.

20. The vector of claim 19, wherein the recombinant vector particle comprises human immunodeficiency virus type 1 Gag, Pol, and Env polypeptides.

21. The vector of claim 19, wherein the recombinant vector particle comprises human immunodeficiency virus type 1 Gag and Pol polypeptides, and vesicular somatitis virus Env polypeptides.

22. The vector of claim 8, wherein the vector is contained in a recombinant vector particle.

23. The vector of claim 22, wherein the recombinant vector particle comprises human immunodeficiency virus type 1 Gag, Pol, and Env polypeptides.

24. The vector of claim 22, wherein the recombinant vector particle comprises human immunodeficiency virus type 1 Gag and Pol polypeptides, and vesicular somatitis virus Env polypeptides.

* * * * *